United States Patent
Huh et al.

(10) Patent No.: US 11,453,848 B2
(45) Date of Patent: Sep. 27, 2022

(54) FIBROSIS MODEL ON A CHIP

(71) Applicant: THE TRUSTEES OF THE UNIVERSITY OF PENNSYLVANIA, Philadelphia, PA (US)

(72) Inventors: Dongeun Huh, Villanova, PA (US); Mark Mondrinos, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/748,087

(22) PCT Filed: Jul. 27, 2016

(86) PCT No.: PCT/US2016/044313
§ 371 (c)(1),
(2) Date: Jan. 26, 2018

(87) PCT Pub. No.: WO2017/019796
PCT Pub. Date: Feb. 2, 2017

(65) Prior Publication Data
US 2018/0230415 A1 Aug. 16, 2018

Related U.S. Application Data

(60) Provisional application No. 62/348,055, filed on Jun. 9, 2016, provisional application No. 62/348,036, filed (Continued)

(51) Int. Cl.
*G01N 33/50* (2006.01)
*C12M 3/00* (2006.01)
(Continued)

(52) U.S. Cl.
CPC ............. *C12M 21/08* (2013.01); *A61L 27/18* (2013.01); *A61L 27/22* (2013.01);
(Continued)

(58) Field of Classification Search
CPC ........ A61F 2/04; A61F 2/062; A61L 27/3804; A61L 27/3834; C12M 25/14; C61M 21/08
See application file for complete search history.

(56) References Cited

U.S. PATENT DOCUMENTS 9,618,500 B2    4/2017   Giselbrecht et al.
11,008,546 B2   5/2021   Huh et al.
(Continued)

FOREIGN PATENT DOCUMENTS

WO   WO 2014/127250 A1   8/2014
WO   WO 2015/061907 A1   5/2015
WO   WO 2015/138032 A2   9/2015

OTHER PUBLICATIONS

U.S. Appl. No. 15/748,039, filed Jan. 26, 2018.
(Continued)

*Primary Examiner* — Suba Ganesan
(74) *Attorney, Agent, or Firm* — BakerHostetler

(57) ABSTRACT

The presently disclosed subject matter provides a biomimetic organ model, and methods of its production and use. In one exemplary embodiment, the biomimetic organ model can be a multi-layer model including a at least two microchannels and at least one chamber slab with at least one membrane coated with cells disposed between at least one microchannel and the at least one chamber slab. In another exemplary embodiment, the biomimetic organ disease model can be a five-layer model including a first and second microchannel with a membrane-gel layer-membrane coated or encompassing cells disposed between the microchannels. In certain embodiments, at least one device can be coupled to the biomimetic organ model that delivers an agent to at least one microchannel.

16 Claims, 25 Drawing Sheets

Related U.S. Application Data on Jun. 9, 2016, provisional application No. 62/197,444, filed on Jul. 27, 2015.

(51) Int. Cl.

| C12M 1/00 | (2006.01) |
|---|---|
| C12M 1/12 | (2006.01) |
| A61L 27/18 | (2006.01) |
| A61L 27/38 | (2006.01) |
| A61L 27/52 | (2006.01) |
| A61L 27/50 | (2006.01) |
| A61L 27/22 | (2006.01) |
| A61L 27/36 | (2006.01) |
| C08L 83/04 | (2006.01) |
| C12N 5/00 | (2006.01) |
| G09B 23/30 | (2006.01) |
| C12M 3/06 | (2006.01) |

(52) U.S. Cl.
CPC ....... *A61L 27/3633* (2013.01); *A61L 27/3804* (2013.01); *A61L 27/50* (2013.01); *A61L 27/52* (2013.01); *C08L 83/04* (2013.01); *C12M 3/00* (2013.01); *C12M 23/16* (2013.01); *C12M 23/20* (2013.01); *C12M 25/02* (2013.01); *C12M 25/14* (2013.01); *C12M 29/10* (2013.01); *C12N 5/0018* (2013.01); *C12N 5/0062* (2013.01); *C12N 5/0068* (2013.01); *G01N 33/5005* (2013.01); *G01N 33/5044* (2013.01); *G09B 23/30* (2013.01); *G09B 23/306* (2013.01); *C12N 2533/30* (2013.01); *C12N 2533/54* (2013.01); *C12N 2535/00* (2013.01); *C12N 2537/10* (2013.01)

(56) References Cited

U.S. PATENT DOCUMENTS

| 2004/0258571 | A1 | 12/2004 | Lee et al. | |
|---|---|---|---|---|
| 2007/0092550 | A1 | 4/2007 | Lui | |
| 2007/0224677 | A1 | 9/2007 | Neumann | |
| 2010/0279268 | A1 | 11/2010 | Neumann et al. | |
| 2011/0250585 | A1* | 10/2011 | Ingber | C12M 25/02 435/5 |
| 2012/0322097 | A1 | 12/2012 | Charest et al. | |
| 2013/0309771 | A1* | 11/2013 | Gevaert | C12M 25/14 435/397 |
| 2013/0344529 | A1 | 12/2013 | Giselbrecht et al. | |
| 2014/0093905 | A1 | 4/2014 | Ingber et al. | |
| 2014/0147880 | A1 | 5/2014 | Ingber et al. | |
| 2014/0158233 | A1 | 6/2014 | Leslie et al. | |
| 2014/0335496 | A1* | 11/2014 | Grego | G09B 23/306 434/272 |
| 2014/0342445 | A1 | 11/2014 | Ingber et al. | |
| 2014/0356849 | A1 | 12/2014 | Wikswo et al. | |
| 2015/0087004 | A1 | 3/2015 | Chen et al. | |
| 2015/0104812 | A1 | 4/2015 | Grevesse et al. | |
| 2015/0329354 | A1 | 11/2015 | Kato et al. | |
| 2016/0313306 | A1 | 10/2016 | Ingber et al. | |
| 2018/0216058 | A1 | 8/2018 | Huh et al. | |

OTHER PUBLICATIONS

U.S. Appl. No. 15/748,066, filed Jan. 26, 2018.
Bhatia, et al., "Microfluidic organs-on-chips," Nature Biotechnology, 32(8):760-772 (2014).
Cagnin et al., "Overview of Micro- and Nano-Technology Tools for Stem Cell Applications: Micropatterned and Microelectronic Devices," Sensors, 12:15947-15982 (2012).
De Souza Carvalho et al., "Carrier interactions with the biological barriers of the lung: Advanced in vitro models and challenges for pulmonary drug delivery," Advanced Drug Delivery Reviews, 75:129-140 (2014).
Evans et al., "The role of material structure and mechanical properties in cell-matrix interactions," Journal of Materials Chemistry B, 2:2345-2356 (2014).
Golden et al., "Fabrication of microfluidic hydrogels using molded gelatin as a sacrificial element," Lab on a Chip, 7:720-725 (2007).
Huh et al., "Microfabrication of human organs-on-chips," Nature Protocols 8(11):2135-2157 (2013).
Huh et al., "Reconstituting Organ-Level Lung Functions on a Chip," Science, 328:1662-1668 (2010).
International Search Report dated Oct. 21, 2016 in International Application No. PCT/US2016/044321.
International Search Report dated Oct. 5, 2016 in International Application No. PCT/US2016/044313.
International Search Report dated Oct. 7, 2016 in International Application No. PCT/US16/44282.
Jorgensen et al., "Cigarette smoke induces endoplasmic reticulum stress and the unfolded protein response in normal and malignant human lung cells," BMC Cancer 8:229 (2008).
Kelsen et al., "Cigarette Smoke Induces an Unfolded Protein Response in the Human Lung: A Proteomic Approach," American Journal of Respiratory Cell and Molecular Biology 38:541-550 (2008).
Kenche et al., "Cigarette smoking affects oxidative protein folding in endoplasmic reticulum by modifying protein disulfide isomerase," FASEB J. 27:965-977 (2013).
Kramann et al., "Perivasculoar Gli1+ Progenitors Are Key Contributors to Injury-Induced Organ Fibrosis," Cell Stem Cell 16:51-66 (2015).
Neal et al., "Formation of elongated fascicle-inspired 3D tissues consisting of high-density, aligned cells using sacrificial outer molding," Lab Chip, 14:1907-1916 (2014).
Sakar et al., "Formation and optogenetic control of engineered 3D skeletal muscle bioactuators," Lab Chip, 12:4976-4985 (2012).
Wen et al., "Interplay of matrix stiffness and protein tethering in stem cell differentiation," Nature Materials, 13:979-987 (2014).
Wolz et al., "In vitro genotoxicity assay of sidestream smoke using a human bronchial epithelial cell line," Food and Chemical Toxicology, 40:845-850 (2002).
Klein et al., "An improved 3D tetraculture system mimicking the cellular organisation at the alveolar barrier to study the potential toxic effects of particles on the lung," Particle and Fibre Toxicology 10:31 (2013) available from: https://particleandfibretoxicology.biomedcentral.com/articles/10.1186/1743-8977-10-31.
Amendment and Request for Continued Examination (RCE) received for U.S. Appl. No. 15/748,066, dated Nov. 23, 2020.
Annabi, N., et al., "Hydrogel-coated microfluidic channels for cardiomyocyte culture," Lab Chip, vol. 13, May 10, 2013, pp. 3569-3577.
Baker, B.M., et al., "Microfluidics embedded within extracellular matrix to define vascular architectures and pattern diffusive gradients," Lab Chip, Jun. 13, 2013, vol. 13, No. 16, pp. 3246-3252.
Baranski, J.D., et al., "Geometric control of vascular networks to enhance engineered tissue integration and function," PNAS, vol. 110, No. 19, May 7, 2013, pp. 7586-7591.
Bertassoni, L.E., et al., "Hydrogel bioprinted microchannel networks for vascularization of tissue engineering constructs," Lab Chip, vol. 14, No. 13, Jul. 7, 2014, pp. 2202-2211.
Bischel, L.L., et al., "Tubeless microfluidic angiogenesis assay with three-dimensional endothelial-lined microvessels," Biomater., vol. 34, No. 5, Feb. 2013, pp. 1471-1477.
Choi et al., Fabrication of a circular PDMS microchannel for constructing a three-dimensional endothelial cell layer, 36(12), Bioprocess. Biosyst. Eng. (2013).
Esch et al., Characterization of in vitro endothelial linings grown within microfluidic channels, Tiss. Eng. A, 17(23-24)12965-2971 (2011) (Year: 2011).
Final Office Action received for U.S. Appl. No. 15/748,039, dated Apr. 27, 2021.
Final Office Action received for U.S. Appl. No. 15/748,066, dated Aug. 25, 2020.
Hammer, J., et al., A facile method to fabricate hydrogels with microchannel-like porosity for tissue engineering, Tiss. Eng., C, vol. 20, No. 2, Feb. 2014, pp. 169-176.

(56) References Cited

OTHER PUBLICATIONS

He, J., et al., "Fabrication of circular microfluidic network in enzymatically-crosslinked gelatin hydrogel" Mater. Sci. Eng. C, vol. 59, Feb. 2016, No. pp 53-60.

Huh, D., et al., "From 3D cell culture to organs-on-chips" Trends Cell Biol., vol. 21, No. 12, Dec. 2011, pp. 745-754.

Issue Fee Payment received for U.S. Appl. No. 15/748,066, mailed on Apr. 14, 2021.

Jimenez-Torres, J., et al., "LumeNEXT: A Practical Method to Pattern Luminal Structures in ECM Gels" Adv. Healthc. Mater, vol. 5, No. 2, Jan. 2016, pp. 198-204.

Kim, H.J., et al., "Human gut-on-a-chip inhabited by microbial flora that experiences intestinal peristalsis-like motions and flow" Lab Chip, vol. 12, Mar. 18, 2012, pp. 2165-2174.

Li et al. "Macrophages promote benzopyrene-induced tumor transformation of human bronchial epithelial cells by activation of NF-KB and STAT3 signaling in a bionic airway chip culture and in animal models." Oncotarget, vol. 6, No. 11 (Mar. 15, 2015), pp. 8900-8913. (Year: 2015).

Liu, J., et al., "Hydrogels for Engineering of Perfusable Vascular Networks" Int. J. Mol. Sci., vol. 16, Jul. 14, 2015, pp. 15997-16016.

Non-Final Office Action received for U.S. Appl. No. 15/748,066, dated Feb. 28, 2020.

Notice of Allowance received for U.S. Appl. No. 15/748,066, dated Jan. 21, 2021.

Park, J., et al., "Real-time measurement of the contractile forces of self-organized cardiomyocytes on hybrid biopolymer microcantilevers," Anal. Chem., vol. 77, No. 20, Oct. 15, 2005, pp. 6571-6580.

Ramadan, O., et al., "In vitro micro-physiological models for translational immunology" Lab Chip, vol. 15, Dec. 2, 2014, pp. 614-636.

Response to Non-Final Office Action received for U.S. Appl. No. 15/748,066, dated May 26, 2020.

Response to Restriction Requirement received for U.S. Appl. No. 15/748,066, dated Nov. 20, 2019.

Restriction Requirement received for U.S. Appl. No. 15/748,066, dated May 20, 2019.

Rothen-Rutishauser et al. "A Three-Dimensional Cellular Model of the Human Respiratory Tract to Study the Interaction with particles." American Journal of Respiratory Cell and Molecular Biology, vol. 32 (2005), pp. 281-289. (Year: 2005).

Stokol, T., et al., Little Channels, Big Disease Using Microfluidics to Investigate Cancer Metastasis, Conference ASME 2011 9th International Conference on Nanochannels, Microchannels, and Minichannels, May 11, 2012, pp. 655-661.

www.merriam-webster.com/dictionary/tissue (accessed Feb. 24, 2020).

Yeon, J.H., et al., "In vitro formation and characterization of a perfusable three-dimensional tubular capillary network in microfluidic devices," Lab Chip, vol. 12, May 24, 2012, pp. 2815-2822.

Yum, K., et al., "Physiologically relevant organs on chips," Biotechnol. J., vol. 9, No. 1, Jan. 2014, pp. 16-27.

Wang et al. "Live human nasal epithelial cells (hNECs) on chip for in vitro testing of gaseous formaldehyde toxicity via airway delivery," Lab on a Chip, vol. 14 (2014), pp. 677-680. First Published on Nov. 28, 2013. (Year 2013).

\* cited by examiner v.

Gold standard mouse bleomycin model

FIBROSIS MODEL ON A CHIP

CROSS-REFERENCE TO RELATED APPLICATIONS

This application is a U.S. National Phase application under 35 U.S.C. § 371 of International Application No. PCT/US2016/044313, filed on Jul. 27, 2016, which claims priority to U.S. Provisional Application Ser. No. 62/197,444, filed on Jul. 27, 2015, U.S. Provisional Application Ser. No. 62/348,036, filed on Jun. 9, 2016, and U.S. Provisional Application Ser. No. 62/348,055, filed on Jun. 9, 2016, all of which are incorporated by reference herein in their entirety.

STATEMENT OF GOVERNMENT INTEREST

This invention was made with government support under Director's New Innovator Award No. 1DP2HL127720-01 awarded by the National Institute of Health. The government has certain rights in the invention.

BACKGROUND

The structural, functional and environmental complexity of human organs poses certain technical challenges for in vitro investigation of organ physiology and pathology using traditional cell culture models. As a result, research in this area has relied on expensive and time-consuming ex vivo or in vivo animal studies that can often fail to model biological responses in humans. These drawbacks of existing models can limit the understanding and the development of new therapeutic approaches to diseases. Therefore, there is a need for a low-cost, human cell-based alternative to current disease models.

For example, organ fibrosis is a progressive, life-threatening medical condition characterized by excessive deposition of extracellular matrix (ECM) in the connective tissue, leading to impairment of normal organ architecture and function. Despite the increasing prevalence of fibrosis in various fatal diseases, understanding of its development and progression remains rudimentary due to the failure of existing models to recapitulate complex human-relevant fibrotic responses.

One approach to meeting these challenges is to leverage microengineering technologies that provide unprecedented capabilities to control cellular microenvironment with high spatiotemporal precision and to present living cultured cells with external influences and biochemical signals in a more physiologically relevant context. This has led to the development of microengineered biomimetic systems such as "organs-on-chips" that simulate complex organ-level physiology. However, there remains a need for additional physiologically relevant, human cell-based alternatives to model organ disease. However, there remains a need for additional physiologically relevant, human cell-based alternatives to model fibrosis.

SUMMARY

The presently disclosed subject matter provides a biomimetic fibrosis model (e.g., lung, liver, kidney, heart, skin, penile, brain, soft tissue, or joint) and methods of its use. The present disclosure also provides for methods of fabricating the biomimetic fibrosis model. In certain embodiments, the biomimetic fibrosis model contains most of the major cellular constituents of the organ being modeled. The biomimetic fibrosis model can be constructed from any organ from which epithelial/parenchymal, stromal, and vascular cells can be obtained and cultured.

In certain embodiments, the biomimetic fibrosis model can be a multi-layer model which can include a body, at least one membrane, at least one gel layer adjacent to the at least one membrane, at least one layer of cells, and a device coupled to the body that can deliver an agent to the cells. In certain embodiments, a multi-layer model allows the modeling of epithelial and/or parenchymal (e.g., lung epithelial cells, liver hepatocytes, etc. . . . ) compartments in one microchannel, stromal (e.g., extracellular matrix and organ specific such as lung or liver derived, fibroblasts, pericytes, stromal cells etc. . . . ) compartments in a gel layer, and vascular endothelial (e.g., lung or liver endothelial cells) compartments in another microchannel. In certain embodiments, the multi-layer model can include vasculature within the gel layer. In certain embodiments, the stromal compartment can include three-dimensional networks of blood and/or lymphatic vessels that can be perfused with blood, drugs, culture media, cells, toxins, particulates, and other materials. In certain embodiments, the stromal compartment can include microchannels that can be perfused with blood, drugs, culture media, cells, toxin, particulates, and other materials. In certain embodiments, the inner surfaces of the microchannels within the stromal compartment can be coated with vascular or lymphatic endothelial cells. In certain embodiments, at least one layer of cells can further comprise macrophages, dendritic cells, and/or microbial cells. In certain embodiments, the stromal compartment can contain resident immune cells such as macrophages and dendritic cells. In certain embodiments, the cells are derived from healthy organs, tissues and/or body fluids. In certain embodiments, the cells can be derived from diseased organs, tissues and/or body fluids. In certain embodiments, the diseased organ can be chronically diseased. In certain embodiments, the cells can be stem cell-derived cells. In certain embodiments, the cells can be patient-derived disease cells and/or patient-derived stem cells.

In certain embodiments, the multi-layer biomimetic fibrosis model can be a three-layer model which includes a body, membrane, at least one layer of cells, and a device coupled to the body that can deliver an agent to the cells. In certain embodiments, the body can have a first and second microchannel. In certain embodiments, the first microchannel can be situated above the second microchannel. In certain embodiments, the membrane can be disposed between a first and second microchannel. The membrane can have a first and second side, wherein the first side faces a first microchannel and the second side faces a second microchannel. The layer of cells can be disposed on the first side of the membrane. In certain embodiments, the three-layer model further comprises a gel layer attached to the second side of the membrane. In certain embodiments, the cells can be embedded in the gel layer.

In certain embodiments, the multi-layer biomimetic fibrosis model can be a five-layer model which includes a body, membrane, at least one layer of cells, a gel layer, and a device coupled to the body that can deliver an agent to the cells. In certain embodiments, the body can have at least a first and at least a second microchannel. In certain embodiments, the first microchannel can be disposed above the second microchannel. In certain embodiments, at least one membrane can be adjacent to at least one microchannel. In certain embodiments, the first membrane adjacent to a first microchannel can have a first and second side, wherein the first side faces a first microchannel and the second side faces the gel layer. In certain embodiments, the second membrane adjacent to a second microchannel can have a first and second side, wherein the first side faces the gel layer and the second side faces a second microchannel. A layer of cells can be disposed on the first side of the first membrane. A layer of cells can be disposed on the second side of the second membrane. In certain embodiments, a layer of organ epithelial and/or parenchymal cells can be attached to the first side of a first membrane. In certain embodiments, a layer of vascular and/or lymphatic endothelial cells can be attached to the second side of a second membrane. In certain embodiments, a layer of vascular and/or lymphatic endothelial cells can be attached to the first side of a first membrane. In certain embodiments, a layer of organ epithelial cells can be attached to the second side of a second membrane. In certain embodiments, the cells can be embedded in the gel layer.

In certain embodiments, the multi-layer biomimetic fibrosis model can be a three-layer model which includes a body, at least one layer of cells, a gel layer, and a device coupled to the body that can deliver an agent to the cells. In certain embodiments, the body can have at least a first and a second microchannel. In certain embodiments, the first microchannel can be disposed above the gel layer. In certain embodiments, the second microchannel can be disposed under the gel layer. In certain embodiments, a layer of cells can be attached to the upper side of the gel layer. In certain embodiments, a layer of cells can be attached to the lower side of the gel layer. In certain embodiments, the cells can be embedded in the gel layer.

In certain embodiments, the five-layer model further comprises a gel layer disposed within the chamber. In certain embodiments, the chamber can have a width of about 3 mm×about 6 mm×about 1 mm. In certain embodiments, the chamber can have a width larger than 3 mm×about 6 mm×about 1 mm. In certain embodiments, the chamber can have a width larger than 3 mm×about 6 mm×about 1 mm. In certain embodiments, the gel layer can be between each membrane. In certain embodiments, the membrane-gel layer-membrane structure can be disposed between a first and second microchannel.

In certain embodiments, the gel of the multi-layer model can comprise extracellular matrix proteins such as, but not limited to, collagen, fibronectin, laminin, elastin, hyaluronic acid, and/or similar materials. In certain embodiments, the gel can comprise collagen. In certain embodiments, tissue or cells can be embedded in the gel. In certain embodiments, engineered particles can be embedded in the gel. In certain embodiments, sensors can be embedded in the gel. In certain embodiments, actuators can be embedded in the gel. In certain embodiments, the gel layer allows the embedded cells to communicate with one another and/or the layer of cells on the membrane and/or the surface of the gel. In certain embodiments, the membrane layers adjacent to the gel layer dissolve allowing the layer of cells on the membrane to directly interact with the cells embedded in the gel layer.

In certain embodiments, the microchannel replicates the dimensions of the functional units of the organ being modeled (e.g., lung, liver, kidney, heart, skin, penile, brain, soft tissue, or joint). In certain embodiments, the microchannel replicates the dimensions of the airways in the native human lung or liver. In certain embodiments, the first microchannel has a width from about 0.1 mm to about 2 mm. In certain embodiments, the first microchannel has a height from about 0.1 mm to about 2 mm. In certain embodiments, the first microchannel has a length from about 1000 µm to about 30 mm.

In certain embodiments, the membrane of the model can be a porous material. In certain embodiments, the membrane can comprise polyester thin clear fabric, polydimethylsiloxane, polymeric compounds, or natural membranes, wherein the natural membrane comprise collagen, laminin, fibronectin, vitronectin, fibrin, other extracellular matrix proteins, fibroin, or a combination thereof.

In certain embodiments, the gel layer of the model contains the interstitial and/or connective tissue of the organ. In certain embodiments, the gel layer of the model contains muscular tissue of the organ, In certain embodiments, the gel layer of the model contains osseous tissue of the organ. In certain embodiments, the gel layer of the model contains neural tissue of the organ. In certain embodiments, the gel layer of the model contains adipose tissue of the organ. In certain embodiments, the gel layer can further comprise macrophages, dendritic cells, and/or microbial cells.

In certain embodiments, the first microchannel can have culture medium flowing through the microchannel. In certain embodiments, the second microchannel can serve as a reservoir for basal feeding. In certain embodiments, the second microchannel can have culture medium flowing through the microchannel. In certain embodiments, the second microchannel can have cell media held within its reservoir. A device can deliver an agent to at least one microchannel. In certain embodiments, the device can deliver an agent to the first microchannel and/or second microchannel. In certain embodiments, the device can deliver an agent to one of a first or second microchannels. In certain embodiments, the device can deliver the agent to a first microchannel.

In certain embodiments, the agents can be small molecules, hormones, proteins, or peptides. In certain embodiments, the agents can be cells, tissue, functional particles, drug delivery vehicles, miniaturized sensors, or miniaturized actuators. In certain embodiments, the device delivers the agent to the first microchannel and/or second microchannel. In certain embodiments, the device can deliver the agent to the perfusable vascular and/or lymphatic vessels within the gel layer. In certain embodiments, the device can deliver the agent to the microchannels within the gel layer. In certain embodiments, the device can deliver the agent directly to the gel layer. In certain embodiments, the device delivering the agent can be an automated machine.

The presently disclosed subject matter further provides methods for producing a biomimetic fibrosis model. In certain embodiments, the method can include fabricating a body. In certain embodiments, the body can have first and second microchannel disposed therein. In certain embodiments, the method can include inserting a membrane between the first and second microchannels. In certain embodiments, the membrane can have a first side and a second side. In certain embodiments, the method can include adhering a layer of cells to the first side of the membrane. In certain embodiments, the layer of cells comprise epithelial cells (e.g., pulmonary, hepatic, renal, etc. . . . ). In certain embodiments, the method can include integrating macrophage cells among the epithelial cells. In certain embodiments, the method can include attaching a gel layer to the second side of the membrane.

In certain embodiments, the method can include fabricating a body. In certain embodiments, the method of fabricating a body can include inserting a first membrane between the first microchannel disposed within a first channel slab and the chamber disposed within a chamber slab. In certain embodiments, the method of fabricating a body can include inserting a second membrane between the second microchannel disposed within a second channel slab and the chamber disposed within a chamber slab. In certain embodiments, the method of fabricating a body can omit the first membrane and/or second membrane. The first and second membrane can have a first side and a second side. In certain embodiments, the method can include adhering a layer of cells to the first side of the first membrane and/or a layer of cells to the second side of the second membrane. In certain embodiments, the layer of cells comprise epithelial cells (e.g., pulmonary, hepatic, renal, etc. . . . ). In certain embodiments, the layer of cells comprise vascular endothelial (e.g., lung or liver endothelial cells). In certain embodiments, the method can include integrating macrophages, dendritic cells, and/or microbial cells among at least one of the layers. In certain embodiments, the method can include forming a gel layer within the chamber. In certain embodiments, the method can include attaching a gel layer to the chamber.

In certain embodiments, the method can include casting a gel. In certain embodiments, the gel can be composed of collagen. In certain embodiments, tissue or cells can be embedded in the gel.

In certain embodiments, the different layers of the biomimetic organ model can be combined in a modular fashion. In certain embodiments, the method can include chemically bonding the fabricated layers of the biomimetic organ model. In certain embodiments, mechanical binding of the layers of the biomimetic organ model allows the layers of cells to be separated and examined separately, for example, following treatment with the agent. In certain embodiments, mechanically bonding the layers includes a clamp (e.g., a screw clamp). In certain embodiments, the method can include bonding the fabricated layers of the biomimetic organ model using adhesive materials (e.g., double sided tape, polymeric resins, Velcro, etc.). In certain embodiments, the method can include bonding the fabricated layers of the biomimetic organ model using negative pressure (e.g., vacuum).

In certain embodiments, the method can include coupling at least one device to the body that delivers an agent to at least one microchannel. In certain embodiments, the method can include delivering an agent to the first microchannel and/or the second microchannel. In certain embodiments, the method can include delivering an agent to one of the first or second microchannels. In certain embodiments, the method can include delivering a culture medium through the first and/or second microchannel. In certain embodiments, the method can include delivering a culture medium through the first and/or second microchannel and then exchanging the flow of medium to the flow of air (with or without the agent) through the first microchannel. In certain embodiments, the method can include delivering a culture medium through blood or lymphatic vessels formed within the gel layer. In certain embodiments, the method can include delivering an agent to blood and/or lymphatic vessels in the gel layer. In certain embodiments, the method can include delivering a culture medium through microchannels in the gel layer. In certain embodiments, the method can include delivering an agent to microchannels in the gel layer.

In accordance with certain embodiments of the disclosed subject matter, a method of testing the effects of a toxic agent on the layer of cells. In certain embodiments, the method can include placing an agent of interest in one of the first or second microchannels. In certain embodiments, the method can include placing an agent of interest in blood and/or lymphatic vessels and/or microchannels embedded in the gel layer. In certain embodiments, the method can include simulating physiological conditions. In certain embodiments, the method can include measuring pathological responses to the agent. In certain embodiments, the method can include measuring tissue hardening or softening in response to the agent.

In certain embodiments, the platform can model organ injury (e.g., fibrosis). In certain embodiments, the biomimetic organ model can be a model of organ fibrosis. In certain embodiments, an agent can induce or inhibit fibrosis in the biomimetic fibrotic organ model. In certain embodiments, the biomimetic organ model can be a model of inflammatory diseases. For example, the presence of macrophages allows for modeling inflammation.

The presently disclosed subject matter further provides methods of using the disclosed biomimetic organ model. In certain embodiments, the biomimetic organ model can be used for identifying pharmaceutical compositions that can treat or prevent organ disease (e.g., fibrosis). In certain embodiments, the biomimetic organ model can be used for identifying agents harmful to the organ.

DETAILED DESCRIPTION

Figure 1:
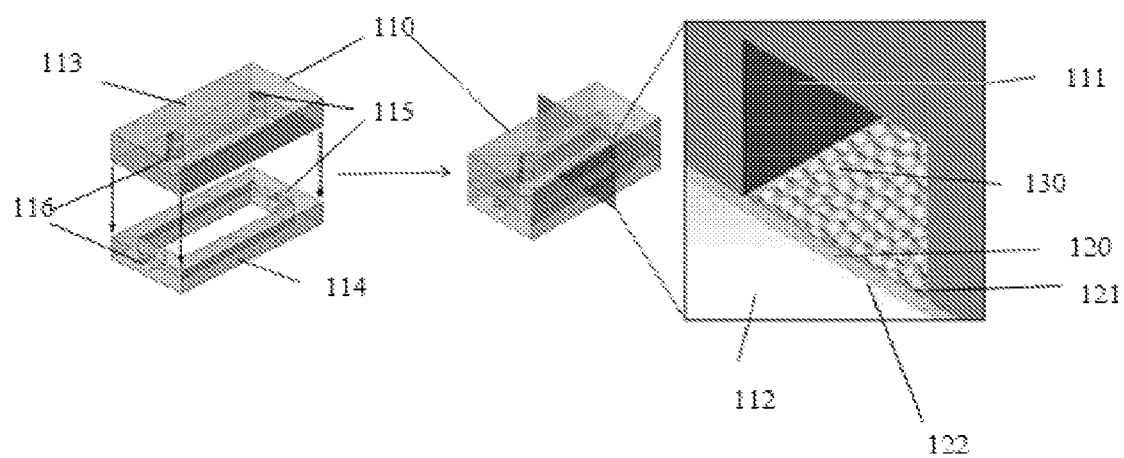
FIG. 1 depicts a microengineered biomimetic multi-layer model subsections (100) according to certain embodiments.
Figure 1:
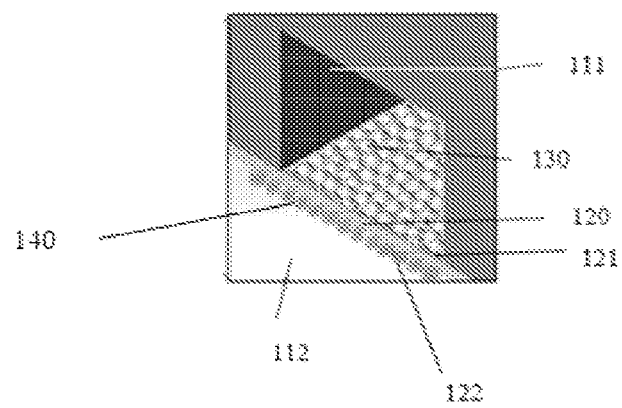

The present disclosure provides a microengineering approach to emulating and probing organ disease processes in a tissue-engineered microenvironment that recapitulates the complexity of each organ (e.g., lung, liver, kidney, heart, penile, uterine, placental, eye, brain, intestine, skin, joints, testis, cervix, ovary, ear, nose, oral cavity, or bone). The disclosed biomimetic organ models can integrate epithelial cells, stromal tissue, vascular components, muscular tissue, neural tissue, and/or immune cells. The incorporation of perfused vascular channels can introduce the circulating immune cell component which can model the recruitment of immune cells under inflammatory conditions.

In certain embodiments, the biomimetic organ model disclosed herein can provide opportunities to develop specialized human disease models that can use patient-derived cells to simulate complex human-specific disease processes for a variety of biomedical, pharmaceutical, toxicological, and environmental applications. For example, in certain embodiments, the biomimetic organ model disclosed herein can be used to study organ pathologies as well as other pathophysiologic processes that can occur in the organ being modeled. In certain embodiments, the biomimetic organ model can be used for identifying pharmaceutical compositions that can treat or prevent organ disease. In certain embodiments, the biomimetic organ model can be used to identify molecular targets and signaling pathways that can be modulated pharmacologically to treat, delay, or prevent disease. Additionally, in certain embodiments, the biomimetic organ model can be used as a screening tool to evaluate the safety and toxicity of environmental exposures (e.g., chemicals, toxins), consumer products, biomedical devices, and drugs, and the transfer of chemicals between compartments (e.g., tissues) of the organ being modeled. In certain embodiments, a multi-organ model comprising multiple organ models connected in series can be used to evaluate the safety and toxicity of environmental exposures (e.g., chemicals, toxins), consumer products, biomedical devices, and drugs, and the transfer of chemicals between the organ and surrounding tissue. In certain embodiments, the biomimetic organ model can be used for identifying agents harmful to the organ.

The present disclosure also provides a microengineering approach to emulating and probing organ disease processes in a tissue-engineered microenvironment that recapitulates the complexity of the organ. In certain embodiments, the platform can model organ fibrosis. In certain embodiments, an agent can induce or inhibit fibrosis in the biomimetic fibrotic organ model. In certain embodiments, the biomimetic organ model can be a model of inflammatory diseases. For example, the presence of macrophages allows for modeling inflammation. In certain embodiments, both resident and circulating immune cells can be integrated into one or more of tissue compartments and/or cell layers.

In certain embodiments, the biomimetic organ model can be a model for organ fibrosis. In certain embodiments, the fibrosis model entails measuring fibroblast proliferation, fibroblast ECM production, and/or stiffening of the gel containing the cells and/or tissue, among other specific cellular-level outputs such as the expression of disease-relevant genes and proteins. The model for organ fibrosis allows for the study of changes in a stromal tissue corresponding to the development of fibrosis in the same way that a piece of solid organ from an animal or human can be analyzed, with the added benefit of modularity that makes separation of tissue layers routinely achievable, a process which requires surgical expertise and dissection microscopy to perform using organs harvested from animals. For example, each tissue layer in the model can be separately fixed, stained and examined by microscopy, or subjected to lysis buffers for the purpose of isolating proteins or nucleic acid to perform biochemical and/or molecular biological analyses. In another example, the model tissue can be isolated from the biomimetic organ model and processed for analysis of its mechanical properties such as stiffness, viscoelasticity, and ECM architecture.

Biomimetic Multi-Layer Fibrosis Model

The presently disclosed subject matter provides a biomimetic multi-layer organ model. The term "layer" includes microchannel layers, gel layers, and membranes. The biomimetic multi-layer organ model can be used to model organs such as, but not limited to, lung, liver, kidney, heart, vagina, cervix, skin, penile, brain, soft tissue, or joint. In certain embodiments, the biomimetic organ model contains the number of layers needed to model the appropriate number of tissue types. In certain embodiments, the biomimetic organ model contains at least 3, at least 4, at least 5, at least 6, at least 7, at least 8, at least 9, or at least 10 layers. In certain embodiments, the biomimetic organ model contains 3, 4, 5, 6, 7, 8, 9, or 10 layers. In certain embodiments, the biomimetic organ model contains 3 layers. In certain embodiments, the biomimetic organ model contains 4 layers. In certain embodiments, the biomimetic organ model contains 5 layers. In certain embodiments, the biomimetic multi-layer organ model includes one or more feeding channels that are not seeded with cells. In certain embodiments, the body further includes one or more microfabricated openings or ports, providing access for inoculation and harvest of cells and agents from any given compartment.

The presently disclosed subject matter provides a biomimetic multi-layer fibrosis model. For the purpose of illustration and not limitation, FIG. 1 provides an exemplary biomimetic four-layer fibrosis model 100. In certain embodiments, the biomimetic fibrosis model can include a first channel slab 113, a second channel slab 114, and a membrane 120. In certain embodiments, the first channel slab 113 and a second channel slab 114 can include a first microchannel 111 and second microchannel 112, respectively, disposed thereon. In certain embodiments, the biomimetic fibrosis model can include a first channel slab 113, a second channel slab 114, a membrane 120, and a gel layer attached to the second side of the membrane 122. A lower reservoir slab can encase the gel. In short term experiments (8 days vs. up to 4 weeks) such as the one pictured in the disclosed embodiment, the gel may not be bound on all sides, with stromal ECM production in response to smoke exposure via the epithelial-seeded microchannel being the primary output.

For the purpose of illustration and not limitation, FIG. 2 (A and B) provides an exemplary biomimetic five-layer fibrosis model 200. In certain embodiments, the first channel slab 210 and a second channel slab 220 can include a first microchannel 211 and second microchannel 221, respectively, disposed thereon. In certain embodiments, the chamber slab 230 can include a chamber 231, disposed thereon. In certain embodiments, the biomimetic fibrosis model can include a first channel slab 210, a second channel slab 220, a chamber slab 230, a first membrane 240, a second membrane 250, and a gel layer 260.

Channel Slabs

For the purpose of illustration and not limitation, the first channel slab and the second channel slab can include at least one channel in each channel slab. In certain embodiments, the first and second channel slabs can each include additional microchannels (e.g., two, three, four, or more, total channels) disposed thereon. In certain embodiments, for every channel in the first channel slab there is a channel in the second channel slab in the same location.

In certain embodiments, each microchannel will have at least one membrane disposed therebetween (e.g., between the first channel slab 113 and the second channel slab 114). In certain embodiments, each microchannel will have at least one membrane (e.g., first membrane and optionally second membrane) and a gel layer disposed therebetween (e.g., between the first channel slab 210 and the second channel slab 220).

In certain embodiments, at least one membrane can dissolve, in which case the cells grown on the membrane would directly contact the gel layer. In certain embodiments, the first membrane and second membrane are absent (i.e., cells can be cultured directly on the gel layer without the intervening membranes).

In certain embodiments, the size of the microchannels can replicate the dimensions of the native human organ being modeled (e.g., lung, liver, kidney, heart, skin, penile, brain, soft tissue, or joint). For example, the size of the microchannels can replicate the dimensions of the airways in the native human lung, liver, or skin.

In certain embodiments, the microchannel can be as high as it is wide and/or as it is long. In certain embodiments, the microchannel the height, width, and/or length are different. In certain embodiments, the height and/or width can change along the length of the biomimetic organ model.

In certain embodiments, the height, width, or length of the microchannels can separately be from about 0.01 nm to about 1 cm. In certain embodiments, the height, width, or length of the microchannels can separately be from about 0.02 nm to about 8 mm, about 0.04 nm to about 6 mm, about 0.06 nm to about 4 mm, about 0.08 nm to about 2 mm, about 0.1 nm to about 1 mm, about 0.2 nm to about 800 µm, about 0.4 nm to about 600 µm, about 0.6 nm to about 400 µm, about 0.8 nm to about 200 µm, about 1 nm to about 100 µm, about 2 nm to about 80 µm, about 4 nm to about 60 µm, about 6 nm to about 40 µm, about 8 nm to about 20 µm, about 10 nm to about 10 µm, about 20 nm to about 8 µm, about 40 nm to about 6 µm, about 60 nm to about 4 µm, about 80 nm to about 2 µm, about 100 nm to about 1 about 200 nm to about 0.8 µm, or about 400 nm to about 0.6 µm.

In certain embodiments, the height, width, or length of the microchannels can separately be from about 0.1 mm to about 2 mm wide. In certain embodiments, the height, width, or length of the microchannels can separately be from about 0.5 mm to about 1 mm. In certain embodiments, the height, width, or length of the microchannels can separately be from about 0.5 mm to about 2 mm. In certain embodiments, the height, width, or length of the microchannels can separately be from about 1 mm to about 2 mm. In certain embodiments, the height, width, or length of the microchannels can separately be from about 0.6 mm to about 1.9 mm, from about 0.7 mm to about 1.8 mm, from about 0.8 mm to about 1.7 mm, from about 0.9 mm to about 1.6 mm, from about 1 mm to about 1.5 mm, or from about 1.2 mm to about 1.4 mm. In certain embodiments, the height, width, or length of the microchannels can separately be at least about 0.5 mm, at least about 0.75 mm, at least about 1 mm, at least about 1.25 mm, at least about 1.5 mm, at least about 1.75 mm, or at least about 2 mm. In certain embodiments, the height and/or width of the microchannels can separately be about 10 mm and the length of the microchannels can be about 10 cm. In certain embodiments, the height, width, or length of the microchannels can separately be about 100 µm to about 500 µm. In certain embodiments, the height, width, or length of the microchannels can separately be about 100 µm to about 400 µm. In certain embodiments, the height, width, or length of the microchannels can separately be about 100 µm to about 300 µm. In certain embodiments, the height, width, or length of the microchannels can separately be about 100 µm to about 200 µm. In certain embodiments, the height, width, or length of the microchannels can separately be about 110 µm to about 190 µm, about 120 µm to about 180 µm, about 130 µm to about 170 µm, or about 140 µm to about 160 µm.

In certain embodiments, the first and second microchannel can have the same dimensions. In certain embodiments, the first and second microchannel can have the different dimensions. In certain embodiments, the microchannels can be each separately about 0.01 nm to about 1 cm wide; about 0.01 nm to about 1 cm high and 0.01 nm to about 1 cm long. In certain embodiments, the microchannels can be each separately about 0.1 mm to about 2 mm wide; about 0.1 mm to about 2 mm high; and about 1 mm to about 10 mm long. In certain embodiments, the microchannel can be about 1 mm wide×about 1 mm high. In certain embodiments, the microchannel can be about 2 mm wide×about 2 mm high. In certain embodiments, the microchannel decrease size as the organ cavity does (e.g, decrease in size as airways in the lung do). For example, one end of the microchannel can be smaller than the other end.

In certain embodiments, for every microchannel in the first channel slab there are the same number of microchannels in each additional channel slab. In certain embodiments, each channel slab can have a different number of microchannels. In certain embodiments, each channel slab can have microchannels in the same corresponding locations. In certain embodiments, each channel slab can have microchannels in different locations.

In certain embodiments, the microchannels can be rectangular, trapezoidal, round, oval, semi-circular or semi-elliptical shaped, semi-circular and square combination.

The number of channels and layouts of the channels, including shape and dimensions, can vary based on the design of the first channel slab and/or additional channel slabs. In certain embodiments, each microchannel will have generally similar dimensions. In certain embodiments, the microchannels will have different dimensions.

In certain embodiments, the channel slabs can be made of any suitable material, for example and without limitation, glass, metal, alloy, plastic, wood, paper, and polymer. Suitable polymers include, but are not limited to, PDMS. In certain embodiments, the channel slabs can be made of any suitable material that can be molded by lithography, 3D printed or in any other way fabricated into the desired shape and dimensions. In certain embodiments, the each channel slab is made from the same material. In certain embodiments, the each channel slab is made from different materials.

Chamber Slab

Figure 2A:
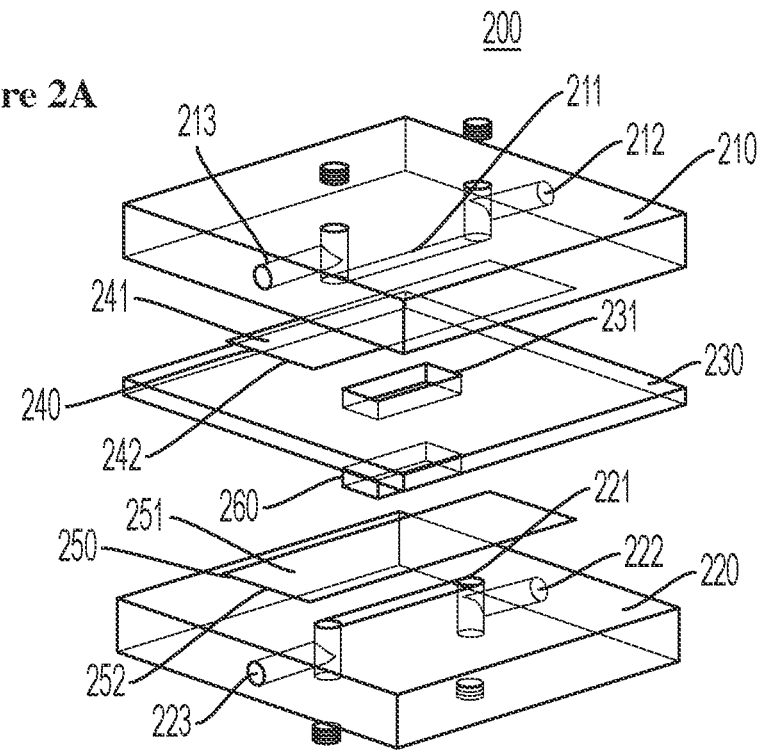
FIG. 2A-B depicts (FIG. 2A) a microengineered biomimetic five-layer model subsections (200) according to certain embodiments and (FIG. 2B) a packaged microengineered biomimetic five-layer model according to other certain embodiments.
Figure 2B:
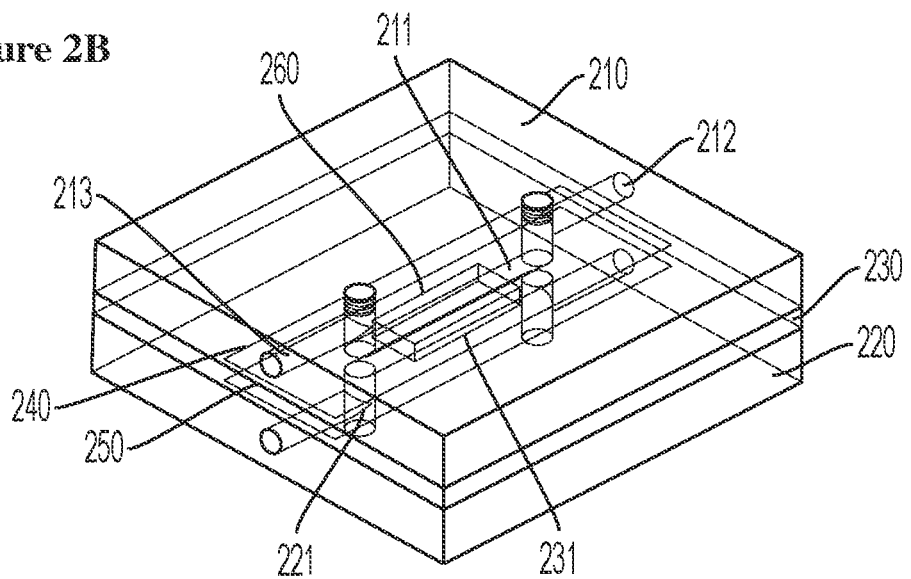

The chamber slab includes a chamber disposed thereon. In certain embodiments, the size of each chamber can replicate the dimensions of stromal tissues relevant to the native organ being modeled. For the purpose of illustration and not limitation, the chamber slab 230 can include a chamber 231, disposed thereon (FIGS. 2A and B).

In certain embodiments, the chamber slab can include more than one chamber (e.g., two, three, four, or more) disposed thereon, with each having a gel layer disposed therein. In certain embodiments, there is a chamber for each microchannel in the first channel slab. In certain embodiments, there are a different number of chambers than microchannels in the first channel slab. The number of chambers, including shape and dimensions, can vary based on the design of the chamber slab.

In certain embodiments the chamber can be about 1 mm to about 5 mm wide. In certain embodiments the chamber can be about 1.2 mm to about 4.8 mm, 1.4 mm to about 4.6 mm, about 1.6 mm to about 4.4 mm, about 1.8 mm to about 4.2 mm, about 2 mm to about 4 mm, about 2.2 mm to about 3.8 mm, about 2.4 mm to about 3.6 mm, about 2.6 mm to about 3.4 mm wide, or about 2.8 mm to about 3.2 mm. In certain embodiments, the chamber has a width of about 3 mm. In certain embodiments, the chamber has a width of about 15 mm.

In certain embodiments the chamber can be about 0.1 mm to about 2 mm high. In certain embodiments the chamber can be about 0.2 mm to about 1.8 mm, about 0.4 mm to about 1.6 mm, about 0.6 mm to about 1.4 mm, or about 0.8 mm to about 1.2 mm high. In certain embodiments, the chamber has a height of about 1 mm. In certain embodiments, the chamber has a height of about 3 mm.

In certain embodiments, the chamber can be about 2 mm to about 10 mm long. In certain embodiments the chamber can be about 2.5 mm to about 9.5 mm, about 3 mm to about 9 mm, about 3.5 mm to about 8.5 mm, about 4 mm to about 8 mm, about 4.5 mm to about 7.5 mm, about 5 mm to about 7 mm, or about 5.5 mm to about 6.5 mm long. In certain embodiments, the chamber has a length of about 6 mm. In certain embodiments, the chamber has a length of about 10 cm.

For the purpose of illustration and not limitation, the chamber (e.g., 231) can be about 3 mm×about 6 mm×about 1 mm.

In certain embodiments, the chamber can be rectangular, trapezoidal, round, oval, semi-circular or semi-elliptical shaped, semi-circular and square combination. In certain embodiments, the geometry of the chamber changes depending on the shape of at least one of the microchannels.

In certain embodiments, each chamber will have generally similar dimensions. In certain embodiments, each chamber will have different dimensions. In certain embodiments, each chamber slab can be made of any suitable material, for example and without limitation, glass, metal, alloy, plastic, wood, paper, and polymer. In certain embodiments, each chamber slab can be made of the same or different material.

In certain embodiments, the gel layer can contain materials encapsulating biochemical payloads (e.g., drug). In certain embodiments, the gel layer can contain emulsions. In certain embodiments, the gel layer can contain magnetic materials. In certain embodiments, the gel layer can contain exothermic or endothermic materials. In certain embodiments, the gel layer can contain light emitting or absorbing materials. In certain embodiments, the gel layer can contain mechanically actuatable materials. In certain embodiments, the gel layer can contain electrically actuatable materials.

In certain embodiments, the gel layer can contain perfusable hollow tubes. In certain embodiments, the hollow tubes can be perfused with culture media, blood, artificial blood, and other fluids. In certain embodiments, the hollow tubes in the gel layer can be coated with endothelial cells. In certain embodiments, the stromal compartment can contain vascular and/or lymphatic tubes formed by self-assembly of endothelial cells embedded in the matrix gel. In certain embodiments, the gel layer can contain hollow cavities.

In certain embodiments, the chamber slabs can be made of any suitable material, for example and without limitation, glass, metal, alloy, plastic, wood, paper, and polymer. Suitable polymers include, but are not limited to, PDMS. In certain embodiments, the channel slabs can be made of any suitable material that can be molded by lithography, 3D printed or in any other way fabricated into the desired shape and dimensions. In certain embodiments, the each chamber slab is made from the same material. In certain embodiments, each chamber slab is made from different materials.

In certain embodiments, the gel layer can be attached to the second side of the membrane separating a microchannel from an underlying reservoir channel, rather than being placed into the chamber.

Membranes

In certain embodiments, there is a membrane for each microchannel. In certain embodiments, there is one membrane for multiple microchannels. In certain embodiments, a microchannel does not have a corresponding membrane.

In certain embodiments, cells are grown on one side of the membrane. In certain embodiments, cells are grown on both sides of the membrane.

In certain embodiments, the each membrane can each independently can have about 0.4 µm to about 10 µm pores. In certain embodiments, the pores have a diameter from about 0.5 µm to about 9 µm, about 0.6 µm to about 8 µm, about 0.7 µm to about 7 µm, about 0.8 µm to about 6 µm, about 0.9 µm to about 5 µm, about 1 µm to about 4 µm, about 1.5 µm to about 3.5 µm, or about 2 µm to about 3 µm. In certain embodiments, the pores can be any suitable size. In certain embodiments, the pores can have varying pore sizes.

In certain embodiments, the thickness of the membrane can be about 1 µm to about 1 mm. In certain embodiments, the thickness of the membrane can be about 50 µm to about 950 µm, about 100 µm to about 900 µm, about 150 µm to about 850 µm, about 200 µm to about 800 µm, about 250 µm to about 750 µm, about 300 µm to about 700 µm, about 350 µm to about 650 µm, about 400 µm to about 600 µm, or about 450 µm to about 550 µm. In certain embodiments, the thickness of the membrane can be about 100 nanometers to about 5 µm. In certain embodiments, the thickness of the membrane can be about 200 nanometers to about 4 µm, about 300 nanometers to about 3 µm, about 400 nanometers to about 2 µm, about 500 nanometers to about 1 µm, about 600 nanometers to about 900 nanometers, or about 700 nanometers to about 800 nanometers. In certain embodiments, the thickness of the membrane can be about 5 µm to about 100 µm. In certain embodiments, the thickness of the membrane can be about 10 µm to about 90 µm, about 20 µm to about 80 µm, about 30 µm to about 70 µm, about 40 micros to about 60 µm. In certain embodiments, the thickness of the membrane is at least about 5 µm, at least about 10 µm, at least about 20 µm, at least about 30 µm, at least about 40 µm, at least about 50 µm, at least about 60 µm, at least about 70 µm, at least about 80 µm, at least about 90 µm, or at least about 100 µm. In certain embodiments, the membrane can include porous portions and non-porous portions.

For the purpose of illustration and not limitation, FIG. 1 provides an exemplary biomimetic three-layer organ model 100 in which the membrane 120 can be disposed between the first microchannel 111 and the second microchannel 112. In certain embodiments, the membrane 120 can have a first side 121 and a second side 122. In certain embodiments, the first microchannel 111 and the second microchannel 112 can be in fluid communication through the membrane 120. In certain embodiments, the first microchannel 111 and the second microchannel 112 can be in fluid communication through the membrane 120 and a gel layer attached to the second side of the membrane 122. In certain embodiments, the membrane 120 can dissolve, in which case the cells grown on the first side of the membrane 121 and the second side of the membrane 122 would directly contact.

For the purpose of illustration and not limitation, FIG. 2 (A and B) provides an exemplary biomimetic five-layer organ model 200 in which the first membrane 240 can be disposed between the first microchannel 211 and the chamber 231 such that the first microchannel 211 and the gel layer 260 can be in fluid communication through the first membrane 240. In certain embodiments, the first membrane 240 can have a first side 241 and a second side 242. In certain embodiments, the second membrane 250 can be disposed between the second microchannel 221 and the chamber 231 such that the second microchannel 221 and the gel layer 260 can be in fluid communication through the second membrane 250. In certain embodiments, the second membrane 250 can have a first side 251 and a second side 252. In certain embodiments, the first microchannel 211 and the second microchannel 221 can be in fluid communication through the first membrane 240, the gel layer 260, and the second membrane 250. In certain embodiments, the first microchannel 211 and the second microchannel 221 can be in fluid communication through the first membrane 240 and the gel layer 260. In certain embodiments, the first membrane 240 and/or second membrane 250 can dissolve, in which case the cells grown on the first membrane 240 and/or second membrane 250 would directly contact the gel layer 260. In certain embodiments, the first microchannel 211 and the second microchannel 221 can be in fluid communication through the gel layer 260 (i.e., no membranes present).

Elimination of the membrane can create a direct contact between the epithelial and/or endothelial cells and the stromal gel layer. Elimination of the membranes can allow transmigration studies, in which cells need to traverse the membrane barriers, to be conducted using the organ models.

In certain embodiments, each membrane can each independently be a thin clear polyester fiber, a polyester membrane, a polytetrafluoroethylene membrane, an elastomeric (e.g., poly(dimethylsiloxane) (PDMS), polyurethane) membrane, a paper membrane, an extracellular matrix membrane, or a natural membrane derived from other biological sources. In certain embodiments, the natural membrane may include collagen, laminin, any combination thereof, and or any ECM material or natural biopolymer that can be acquired, including biopolymers such as chitosan and alginate. The selection of the pore sizes, materials and other features of the membrane can be varied based on the design of the biomimetic organ model, the experimental goals, or other suitable motivations. The dissolving membranes can include water soluble materials (e.g., alginate and Poly-vinyl alcohol (PVA)). In certain embodiments, the dissolving membranes can include non-crosslinked ECM membranes (e.g., membranes derived from Matrigel) that only provide a transient barrier following rehydration.

Cell Layers

In certain embodiments, the biomimetic organ model contains most of the major cellular constituents of the human organ. For example, but not limited to, the layer of cells can be lung, liver, kidney, heart, penile, uterine, placental, eye, brain, intestine, skin, joints, testis, cervix, ovary, ear, nose, oral cavity, or bone derived cells. In certain embodiments, the first or second cell layer can have an artificially induced pathology (e.g., fibrosis). In certain embodiments, the cell layers can be monolayers.

For the purpose of illustration and not limitation, FIG. 1 provides an exemplary biomimetic three-layer organ model 100 in which a first layer of cells 130 can be grown on the first side of the membrane 121 and/or the second side of the membrane 122. In certain embodiments, a first layer of cells 130 can be grown on the first side of the first membrane 130 and a second layer of cells 140 can be grown on the second side of the second membrane 122.

For the purpose of illustration and not limitation, FIG. 1 provides an exemplary biomimetic three-layer organ model 100 comprising a gel layer attached to the second side of the membrane 122, which can be comprised of collagen matrix and/or organ specific fibroblasts/pericytes/stromal cells (e.g., lung or liver derived) as described further below. In certain embodiments, tissue or cells can be embedded in the gel layer. In certain embodiments, the gel layer allows the embedded cells to communicate with the layer of cells on the membrane 120.

For the purpose of illustration and not limitation, FIG. 2 (A and B) provides an exemplary biomimetic five-layer organ model 200 in which a first layer of cells can be grown on the first side of the first membrane 241 and/or the second side of the second membrane 252. In certain embodiments, a first layer of cells can be grown on the first side of the first membrane 241 and a second layer of cells can be grown on the second side of the second membrane 252.

For the purpose of illustration and not limitation, FIG. 2 (A and B) provides an exemplary biomimetic five-layer organ model 200 comprising a gel layer 260, which can be comprised of collagen matrix and/or organ specific fibroblasts/pericytes/stromal cells (e.g., lung or liver derived) as described further below. In certain embodiments, tissue or cells can be embedded in the gel layer 260. In certain embodiments, the gel layer 260 allows the embedded cells to communicate with the layer of cells on the first membrane 240 and/or the second membrane 250.

In certain embodiments, a layer of cells can be attached to one side or both sides of a membrane. In certain embodiments, a layer of cells can be attached to one side of a membrane that is opposite from the gel layer. In certain embodiments, a layer of cells can be attached to one side of a membrane that is facing the gel layer.

In certain embodiments, a layer of organ epithelial cells can be attached to the first side of a first membrane. In certain embodiments, a layer of vascular endothelial cells can be attached to the second side of a second membrane. In certain embodiments, a layer of vascular endothelial cells can be attached to the first side of a first membrane. In certain embodiments, a layer of organ epithelial cells can be attached to the second side of a second membrane.

In certain embodiments, the layer of cells can be epithelial cells (e.g., lung epithelial cells or liver hepatocytes). In certain embodiments, the epithelial cells can be from all compartments of the organ. In certain embodiments, the epithelial cells are derived from human or animal tissue. In certain embodiments, the epithelial cells can be from healthy human or animal organ tissue. In certain embodiments, the epithelial cells can be from diseased human or animal organ tissue (e.g., fibrotic). In certain embodiments, the diseased organ can be chronically diseased. In certain embodiments, the layer of cells can further comprise macrophages, dendritic cells, and/or microbial cells.

In certain embodiments, the layer of cells can be endothelial cells (e.g., pulmonary or hepatic microvascular endothelial cells). In certain embodiments, the endothelial cells can be large vessel endothelial cells, arterial endohtelial cells, venous endothelial cells. In certain embodiments, the endothelial cells can be lymphatic endothelial cells. In certain embodiments, the endothelial cells are derived from human or animal tissue. In certain embodiments, the endothelial cells can be from healthy human or animal organ tissue. In certain embodiments, the endothelial cells can be from diseased human or animal organ tissue (e.g., fibrotic). In certain embodiments, the diseased organ can be chronically diseased. In certain embodiments, the layer of cells can further comprise macrophages, dendritic cells, and/or microbial cells.

In certain embodiments, the multi-layer model further comprises a gel layer embedded with cells disposed within the chamber. In certain embodiments, the gel layer of the model contains the interstitial and/or connective tissue or cells of the organ. For example, the gel of the model can comprise extracellular matrix proteins such as, but not limited to, collagen, fibronectin, laminin, elastin, hyaluronic acid, and/or similar materials. In certain embodiments, the gel can comprise collagen. Any collagen subtype can be used (e.g., collagen I, II, IV, and accessible collagen). Any extracellular matrix material can be used, including any organotypic mixture from tissues/organs. In certain embodiments, fibronectin, vitronectin, laminins, proteoglycans, tenascin (e.g., extracellular matrix glycoproteins) etc. can be used (e.g., tenascin-C, -R, -X, and/or -W). In certain embodiments, the gel layer can further comprise macrophages, dendritic cells, and/or microbial cells.

In certain embodiments, tissue or cells can be embedded in the gel. The gel layer allows the embedded cells to communicate with the layer of cells on the membrane. In certain embodiments, the membrane layers adjacent to the gel layer dissolve allowing the layer of cells on the membrane to directly interact with the cells embedded in the gel.

In certain embodiments, the cells embedded in the gel layer can be connective tissue or cells. In certain embodiments, the cells embedded in the gel layer can be stromal cells. The cells embedded in the gel layer can be basal stromal cells, such as, but not limited to, fibroblasts and/or pericytes. In certain embodiments, the cells embedded in the gel layer can be airway and/or vascular smooth muscle cells. In certain embodiments, the cells embedded in the gel layer can be neurons, astrocytes, and microglia cells. In certain embodiments, the cells embedded in the gel layer can be endothelial cells and fibroblasts of any organ. In certain embodiments, the cells embedded in the gel layer can be osteocytes, osteoblasts, and osteoclasts. In certain embodiments, the cells embedded in the gel layer can be adipocytes and/or adipose tissue-derived stem cells. In certain embodiments, the cells embedded in the gel layer can be sertoli cells and Leydig cells. In certain embodiments, the cells embedded in the gel can be cervical smooth muscle cells. In certain embodiments, the cells embedded in the gel can be uterine smooth muscle cells. In certain embodiments, the cells embedded in the gel layer can be dermal papilla cells. In certain embodiments, the cells embedded in the gel layer can be keratocytes, In certain embodiments, the cells embedded in the gel layer can be retinal cells. In certain embodiments, the cells embedded in the gel layer can be dermal papilla cells.

In certain embodiments, the layers of cells can further comprise macrophages, dendritic cells, and/or microbial cells. In certain embodiments, the macrophages can be alveolar, interstitial, intravascular, airway macrophages and/or an immortalized cell line (e.g., THP-1). The macrophages can be harvested from tissue. The macrophages can be generated. In certain embodiments, the macrophages can be generated from blood (e.g., from peripheral blood monocytes). In certain embodiments, the macrophages can be a primary component of the gel layer.

In certain embodiments, such as the embodiment of the four-layer model, the macrophage cells can be added to the epithelial cell layer for channel co-culture at a ratio of about 1 macrophage to about 100 epithelial cells. In certain embodiments, the macrophage cells can be added to the epithelial cell layer at a ratio of about 1 macrophage to about 50 epithelial cells. In certain embodiments, the macrophage cells can be added to the epithelial cell layer at a ratio of about 1 macrophage to about 95 epithelial cells, about 1 macrophage to about 90 epithelial cells, about 1 macrophage to about 85 epithelial cells, about 1 macrophage to about 80 epithelial cells, about 1 macrophage to about 75 epithelial cells, about 1 macrophage to about 70 epithelial cells, about 1 macrophage to about 65 epithelial cells, about 1 macrophage to about 60 epithelial cells, about 1 macrophage to about 55 epithelial cells, about 1 macrophage to about 50 epithelial cells, about 1 macrophage to about 45 epithelial cells, about 1 macrophage to about 40 epithelial cells, about 1 macrophage to about 35 epithelial cells, about 1 macrophage to about 30 epithelial cells, about 1 macrophage to about 25 epithelial cells, about 1 macrophage to about 20 epithelial cells, about 1 macrophage to about 18 epithelial cells, about 1 macrophage to about 16 epithelial cells, about 1 macrophage to about 14 epithelial cells, about 1 macrophage to about 12 epithelial cells, about 1 macrophage to about 10 epithelial cells, about 1 macrophage to about 8 epithelial cells, about 1 macrophage to about 6 epithelial cells, or about 1 macrophage to about 5 epithelial cells. In certain embodiments, similar ratios of macrophages to epithelial cells can be used for co-culture of macrophages with organ-specific fibroblasts in the gel layer.

In certain embodiments, the dendritic cells can be Langerhans cells, interstitial dendritic cells, interdigitating dendritic cells, follicular dendritic cells, and/or circulating dendritic cells. Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid.

In certain embodiments, the microbial cells can be bacteria, yeast, mold, lichens, algae, fungi, actinomycetes and/or protozoa.

In certain embodiments, circulating immune cells (e.g., neutrophils, eosinophils, basophils, lymphocytes, and/or monocytes) can be introduced into the first and/or second microchannel (e.g., 111, 112, 211, 221) via perfusion with the appropriate culture medium. Introduction of immune cells into the first and/or second microchannel can model the recruitment of immune cells under pathological conditions (e.g., inflammatory).

Figure 3:
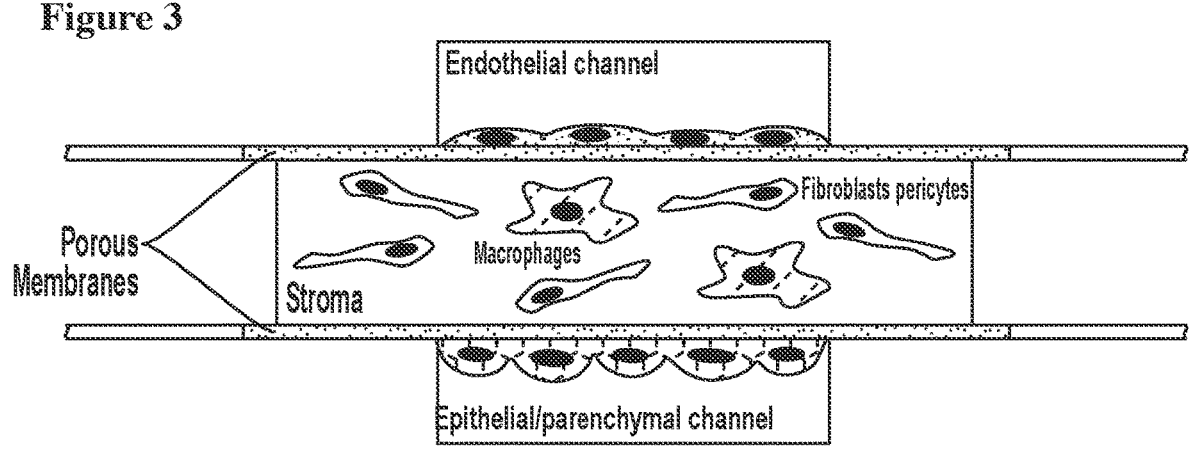
FIG. 3 depicts a schematic of an exemplary approach to the microengineered biomimetic five-layer model cell layer construction.

Referring to FIG. 3 for the purpose of illustration and not limitation, there is provided a exemplary model of the order of the different cell layers of the five-layer model. For example, in FIG. 3, the epithelial cells are grown on the first side of the first membrane and the endothelial cells are grown on the second side of the second membrane while the gel layer incorporates the stromal compartment. In certain embodiments, the exemplary model of FIG. 3 can be used for immune cell transmigration experiments. In certain embodiments, the cells are incorporated in a different order.

For the purpose of illustration and not limitation, the biomimetic organ model can be a lung model containing a portion of the major cellular constituents in the airway niches of the human lung. In certain embodiments, the layer of cells comprises airway epithelial cells. In certain embodiments, the airway epithelial cells can comprise Type I and Type II cells. In certain embodiments, the airway epithelial cells can be from all compartments of the lung, including but not limited to, tracheal epithelial cells, bronchial epithelial cells, small airway epithelial cells and/or alveolar epithelial cells, (e.g., Type I and II cells). In certain embodiments, the second layer of cells can be endothelial cells including pulmonary microvascular endothelial cells such as large vessel endothelial cells, arterial endothelial cells, venous endothelial cells all from lung. In certain embodiments, the second layer of cells can be lymphatic endothelial cells. In certain embodiments, the platform can model all the different segments/depths of the lung. In certain embodiments, the airway epithelial cells can be from healthy human lung. In certain embodiments, the airway epithelial cells can be from a human diseased lung. In certain embodiments, the diseased lung can be chronically diseased. In certain embodiments, the layer of cells can further comprise macrophages, dendritic cells, and/or microbial cells. In certain embodiments, the macrophages can be alveolar, interstitial, intravascular, airway macrophages, and/or an immortalized macrophage cell line (e.g., THP-1).

Cell Culture

In certain embodiments, the cells can be obtained from organ (e.g., lung, liver, kidney, heart, penile, uterine, placental, eye, brain, intestine, skin, joints, testis, cervix, ovary, ear, nose, oral cavity, or bone) tissue. In certain embodiments, the cells can be obtained from a primary culture generated from the organ tissue. Standard techniques of tissue harvesting and preparation can be used.

In certain embodiments, any of the cells can be derived from an immortalized cell line.

In certain embodiments, any of the cells can be stem cell-derived cells.

In certain embodiments, adhering the layer of cells to the first and/or second membrane can include standard approaches of extracellular matrix coating of the membrane, for example, but not limited to the use of fibronectin, prior to seeding of cells. In certain embodiments, adhering the layer of cells to the first side of the membrane can include formation of extracellular matrix hydrogel on the surface of the membrane, for example, but not limited to the use of collagen gel, prior to seeding of cells.

In certain embodiments, to seed the cells, a high density cell suspension can be introduced to the channel and allowed to incubate under static conditions to allow the cells to adhere. In certain embodiments, the cell suspension can be allowed to incubate for 2 to 4 hours. In certain embodiments, the seeding method (e.g., incubation period of the cell suspension) can vary depending on the compartment and/or cell type. In certain embodiments, after the period of attachment flow can be initiated to allow the washing away of unattached cells and beginning the perfused culture stage. In certain embodiments, some cell proliferation can occur to fill out the entire membrane surface. In certain embodiments, cell proliferation is allowed to occur for 2-3 days or longer.

In certain embodiments, the immune cells are obtained from peripheral blood and incorporated into the organ model. For example, peripheral blood monocytes can be obtained to generate the macrophage cells used in the model. In certain embodiments, THP-1 cells are used. In certain embodiments, macrophages can be obtained from patient biopsies. In certain embodiments, the macrophages can be obtained by organ lavages (e.g., but not limited to bronchoalveolar, renal, or vaginal lavages).

In certain embodiments, the macrophages can be introduced into the channel after the epithelial layer has formed. For example, this can be accomplished by pipetting them into the channel. As they differentiate they can adhere to the epithelial cells and can migrate on the epithelial surface. In certain embodiments, inflammatory responses can be assessed by testing the strength of macrophage adherence to the epithelium by washing the channel and assaying the number of macrophages that remain adherent to the epithelium.

In certain embodiments, the stromal cells are derived from a primary cell culture, established cell culture, or an immortalized cell culture. In certain embodiments, the stromal cells are obtained from a biopsied tissue. In certain embodiments, the stromal cells can be derived from patient-derived stem cells such as mesenchymal stem cells, or from pluripotent cells including healthy donor- or disease patient-derived induced pluripotent stem cells.

In certain embodiments, the gel layer contains nutrients to feed the cells. In certain embodiments, the cells in the gel layer obtain nutrients from culture medium from the microchannels or a reservoir. In certain embodiments, the cells obtain nutrients from within the gel and/or from culture medium from the microchannels or a reservoir.

Methods of Fabrication

In certain embodiments, the method can include fabricating a body, the body having microchannel layers and at least one gel layer disposed thereon. The body, including the microchannels layers and gel layers, can be built by any methods known in the art, including, but not limited to, those outlined in Huh et al., Nature Protocols 8:2135-2157 (2013).

In certain embodiments, the different layers of the body can be chemically bonded, i.e., oxygen plasma treatment of PDMS. Chemically bonding can result in cell death; therefore, if the biomimetic organ model is chemically bonded together, the cells can be added to the biomimetic organ model after chemical bonding is complete.

In certain embodiments, the different layers of the body can be mechanically bonded. Mechanical bonding allows the different tissue components to be cultured separately before interfacing them together, so as to engineer the various tissue layers in an isolated context and then stacking them to form the organ (multi-tissue) configuration. In certain embodiments, mechanically bonding the layers includes a clamp. A clamp includes, but is not limited to a screw clamp, cam clamp, spring clamp, binder clip, vice, C-clamp, adjustable hand screw clamp, spring clamp, pipe clamp, bar clamp, parallel clamp, F style clamp, or a threaded rod with one or more fasteners. In certain embodiments, the method can include bonding the fabricated layers of the biomimetic organ model using adhesive materials. Adhesive materials includes, but are not limited to, PDMS glue, double sided tape, hemming tape, removable adhesive fabric, rubber cement, adhesive polymers (e.g., polysulfones, polyethersulfones, polyimides, polyamide-imides, epoxy resins, polyarylene ether ketones such as, chloromethylated polyarylene ether ketones, acryloylated polyarylene ether ketones, and mixtures thereof, preformed polyimides, polyetherimides, polystyrene, and the like and cholromethylated polyethersulfones and acryloylated polyethersulfones). In certain embodiments, the method can include bonding the fabricated layers of the biomimetic organ model using negative pressure (e.g., vacuum).

In certain embodiments, the different layers of the biomimetic organ fibrosis model can be combined in modular fashion according to a desired time sequence. In certain embodiments, the entire biomimetic organ fibrosis model device does not need to assemble at first. For example, each of the layers can be cultured separately for any desired length of time and then subsequently combined to form the complete model.

In certain embodiments, the method can include casting a gel in the chamber of the chamber slab. In certain embodiments, the method can include casting a gel to attach to a single membrane or multiple membranes.

Gel casting can involve any standard method known to one of skill in the art. In certain embodiments, techniques are used to induce surface modification to promote collagen/ECM anchoring. In certain embodiments, the casting of a gel can include sulfo-sanpah treatment of the chamber slab material to promote collagen/ECM anchorage. In certain embodiments, the casting of a gel can include sulfo-sanpah treatment of the membrane material and channel material to promote collagen/ECM anchorage. For example, the surface of the portion of the chamber slab in which the gel layer can be attached to can be treated with sulfo-sanpah and exposed to UV light (for example two times at 5 minutes each).

In certain embodiments, the gel layer can contain perfusable hollow tubes. In certain embodiments, the gel layer can contain hollow cavities. In certain embodiments, tubes and cavities can be formed by several techniques including needle withdrawal and vasculogenesis (e.g., development of an interconnected hollow tubular network by vascular endothelial cells present in the gel layer). According to the needle withdrawal technique, a gel can be formed around a thin needle that is subsequently removed to leave a channel in the gel. According to the vasculogenesis technique, vascular cells can be seeded in a channel interfaced with the gel to grow into the gel, creating a network of perfusable capillaries.

In certain embodiments, the gel is prepared with cells and pipetted onto the chamber. The density of the cells can range from about $1\times10^4$/ml of gel solution cells to $1\times10^8$/ml of gel solution, depending on the experiment and the culture condition of the cells. One of ordinary skill would understand the cell density and culture conditions required for each particular gel layer depending on the goals of the experiment (e.g., lower density normal vs higher density fibrotic tissues).

In certain embodiments, the gel is prepared without cells and pipetted onto the chamber or onto a membrane. If the biomimetic organ model is already bound together, the cells can be placed into one of the channels and transmigrate to populate the empty gel.

In certain embodiments, the surface-anchored hydrogel extends the time before contraction of the gel layer away from the chamber occurs. In certain embodiments, contraction of the surface-anchored hydrogel away from the chamber occurs no earlier than about 2 days, about 3 days, about 4 days, about 5 days, about 6 days, about 7 days, about 8 days, about 9 days about 10 days, about 11 days, about 12 days, about 13 days, about 14 days, about 15 days, about 16 days, about 17 days, about 18 days, about 19 days, or about 20 days. In certain embodiments, contraction of the surface-anchored hydrogel away from the chamber occurs between about 5 and about 20 days, about 6 and about 19 days, about 7 and about 18 days, about 8 and about 17 days, about 9 and 16 days, about 10 and about 15 days, about 11 and about 14 days, or about 12 and about 13 days. In certain embodiments, contraction of the surface-anchored hydrogel away from the chamber occurs no earlier than about 7 days, about 10 days, about 14 days, about 17 days, about 21 days, about 24 days, about 28 days, about 31 days, about 35 days, about 38 days, or about 42 days. In certain embodiments, contraction of the surface-anchored hydrogel away from the chamber occurs no earlier than about 1 week or no earlier than about 2 weeks under fibrotic conditions. In certain embodiments, contraction of the surface-anchored hydrogel away from the chamber occurs no earlier than about 3 weeks or no earlier than about 4 weeks under normal (e.g., non-fibrotic) conditions.

Figure 4:
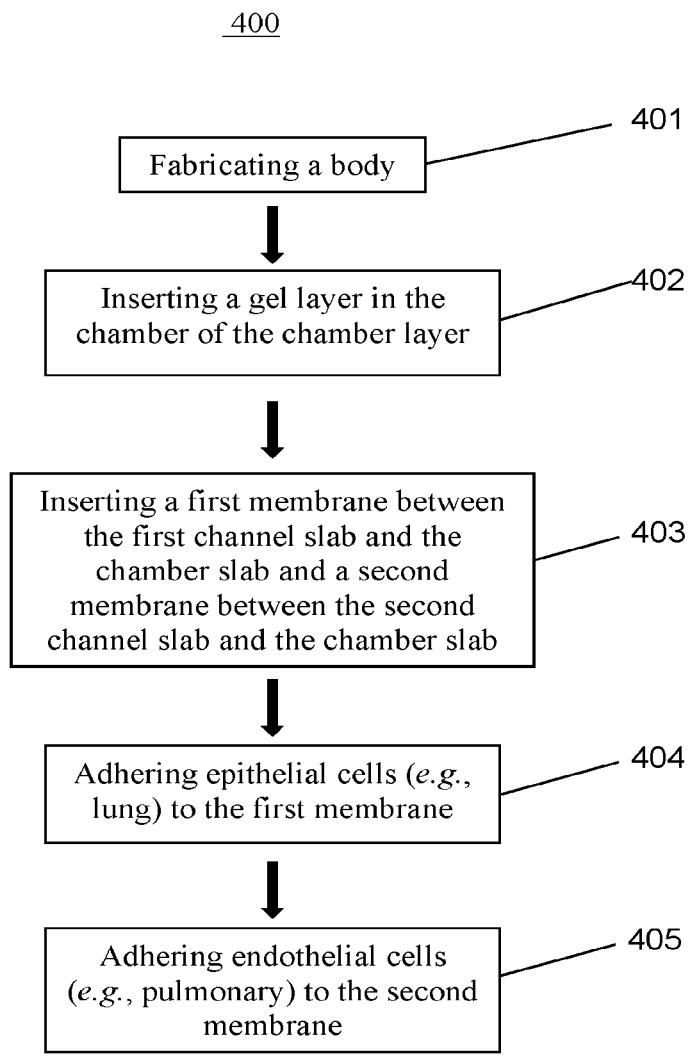
FIG. 4 depicts a schematic representation of an exemplary method according to the disclosed subject matter.

Referring to FIG. 4 for the purpose of illustration and not limitation, there is provided an exemplary method for fabricating a biomimetic five-layer organ model (400). In certain embodiments, the method can include fabricating a first channel slab, a second channel slab, and a chamber slab (401), the first channel slab and second channel slab having a first and second microchannels disposed thereon and the chamber slab having a chamber disposed thereon. In certain embodiments, the method can include casting a gel into the chamber of the chamber slab (402). In certain embodiments, the method can include inserting a first membrane between the first channel slab and the chamber slab and a second membrane between the second channel slab and the chamber slab (403) such that the first and second microchannels can each be in fluid communication with the chamber through the membranes. In certain embodiments, temporary layers can be used to ensure the gel surfaces are flat and it can subsequently be contacted with a membrane-bound channel. The constituents of the gel are described above. In certain embodiments, the method can include adhering a first layer of cells (404) of a first cell type disposed on a first side of the first membrane. In certain embodiments, the method can include adhering a second layer of cells (405) of a second cell type disposed on a second side of the second membrane. In certain embodiments, the first membrane and second membrane are absent (i.e., cells can be cultured directly on the gel layer without the intervening membranes) or the membranes dissolve.

Figure 5:
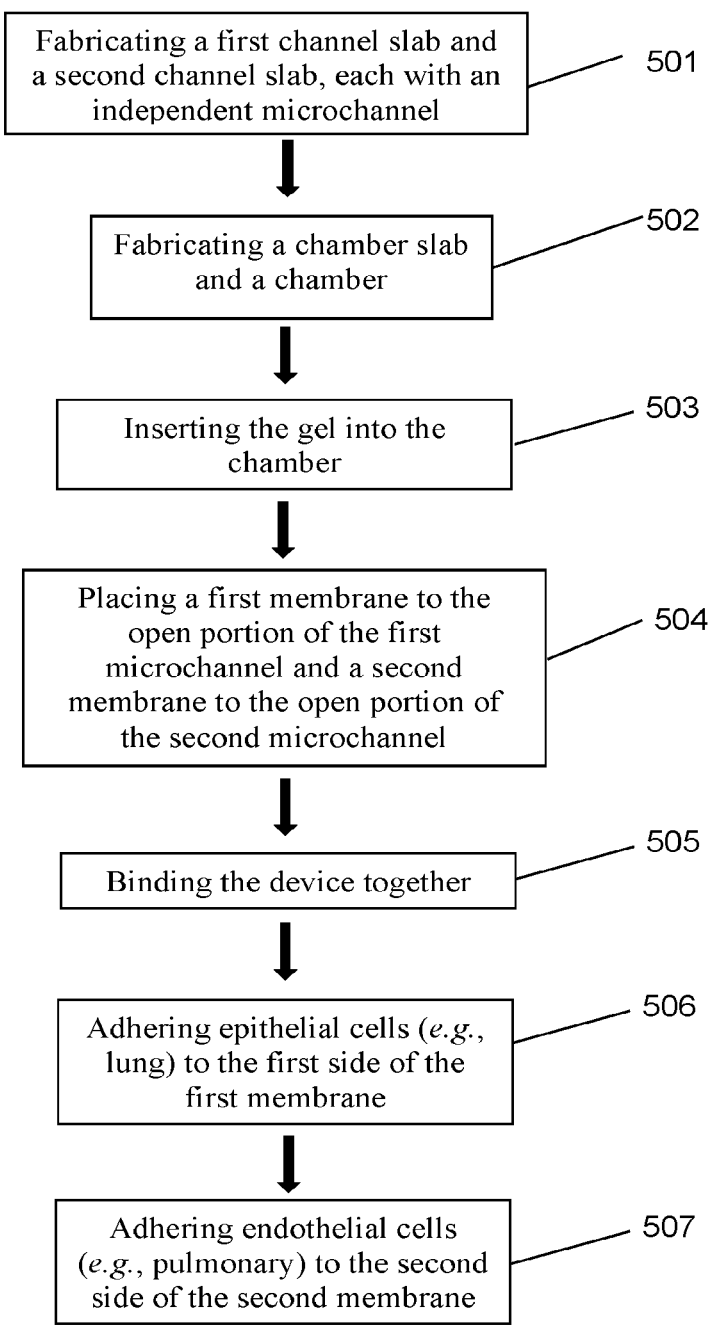
FIG. 5 depicts a schematic representation of an exemplary method according to the disclosed subject matter.

Referring to FIG. 5 for the purpose of illustration and not limitation, there is provided an exemplary method for fabricating a biomimetic five-layer organ model (500). In certain embodiments, the method can include fabricating a first channel slab and a second channel slab (501), wherein each portion has at least one separate microchannel disposed thereon. In certain embodiments, the method can include fabricating a chamber slab (502), wherein the chamber slab has at least one chamber disposed thereon. In certain embodiments, the cells are individually cultured prior to the assembly of the biomimetic organ model. In certain embodiments, the method can include casting a gel layer in the chamber (503). The constituents of the gel are described above. In certain embodiments, the method can include placing a first membrane to the first microchannel and a second membrane to the second microchannel (504). In certain embodiments, the membranes can be fixed to the channel slabs via PDMS stamping or gluing. In certain embodiments, the PDMS glue can be uncured PDMS. In certain embodiments, the membranes can be held to the channel slabs using mechanical means as discussed above. In certain embodiments, the membrane can have a first and second side. In certain embodiments, the slabs containing the first and second microchannels and chamber can be mechanically bonded (505) as discussed above. The first side of the first membrane faces the first microchannel and the second side of the second membrane faces the second microchannel once the biomimetic organ model is assembled. In certain embodiments, the method can include (506) adhering a layer of cells of a first cell type disposed on a first side of the first membrane. In certain embodiments, the method can include (507) adhering a layer of cells of a second cell type disposed on a second side of the second membrane.

Figure 6:
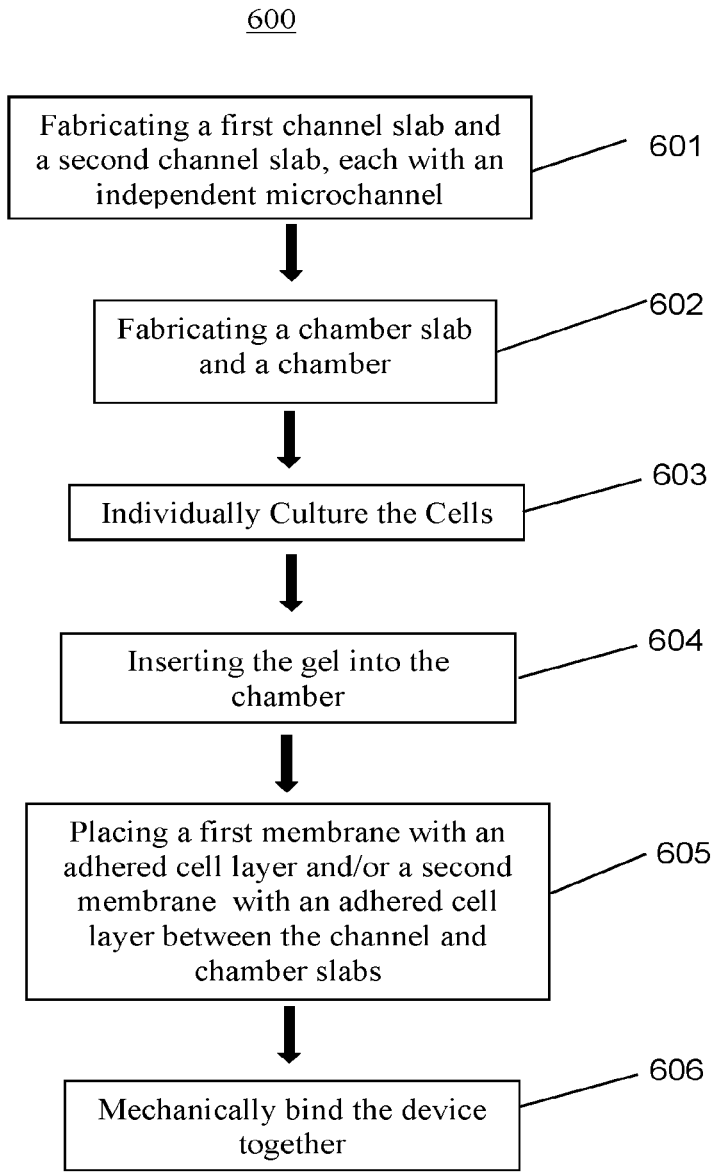
FIG. 6 depicts a schematic representation of an exemplary method according to the disclosed subject matter.

Referring to FIG. 6 for the purpose of illustration and not limitation, there is provided an exemplary method for fabricating a biomimetic five-layer organ model (600). In certain embodiments, the method can include fabricating a first channel slab and a second channel slab (601), wherein each portion has a separate microchannel disposed thereon. In certain embodiments, the method can include fabricating a chamber slab (602), wherein the chamber slab has a chamber disposed thereon. In certain embodiments, the cells are individually cultured prior to the assembly of the biomimetic organ model (603). In certain embodiments, the method can include casting a gel layer in the chamber (604). The constituents of the gel are described above. In certain embodiments, the method can include placing a first membrane over the first microchannel and a second membrane over the second microchannel (605), wherein a layer of cells are adhered to at least one of the membranes. In certain embodiments, the slabs containing the first and second microchannels and chamber can be mechanically bonded (606) as discussed above. The first side of the first membrane faces the first microchannel and the second side of the second membrane faces the second microchannel once the biomimetic organ model is assembled.

In certain embodiments, a device can deliver culture medium to the first and/or second microchannels. In certain embodiments, a device can deliver culture medium to one of the first or second microchannels. In certain embodiments, a device can deliver culture medium to only the second microchannel. In certain embodiments, the device can pump culture medium to the microchannel(s) through a port (e.g., FIG. 2 (e.g., 212 and/or 222)) in the channel slabs, wherein the first opening of the port (e.g., 212 and/or 222) can be to the outside of the channel slabs and the second opening of the port (e.g., 212 and/or 222) can be to the respective microchannel. In certain embodiments, channels from the top and bottom of the channel slabs that lead to the microchannels can be accessed to provide agent and/or culture media to the microchannels. In certain embodiments, access to both the top and sides of the channels can be provided. In certain embodiments, the culture medium leaves the microchannel through an exit port (e.g., 213 and/or 223). In certain embodiments, the device can pump culture medium out of the microchannel(s) through an exit port (e.g., 213 and/or 223), wherein the first opening of the exit port (e.g., 213 and/or 223) opens to the microchannel and the second opening of the exit port (e.g., 213 and/or 223) can be to the outside of the channel slab. In certain embodiments the port (e.g., 212 and/or 222) or exit port (e.g., 213 and/or 223) only connects to one microchannel. In certain embodiments, cell culture media with different constituents can be added to separate microchannels. The cell culture media can be selected based on the type of cell grown on the membrane facing the microchannel. In certain embodiments, the pumping system can draw/pull medium though the channels from a reservoir. In certain embodiments, the pumping system can push medium though the channels from a reservoir. In certain embodiments, perfusion can be achieved without pumps using gravity driven flow. In certain embodiments, a recirculatory flow loop can be used. In certain embodiments, the pumping system can deliver medium from a separate organ module or modules.

In certain embodiments, the second microchannel can have cell media held within its reservoir.

Agent Delivery

In certain embodiments, the agent can be delivered to the first and/or second microchannel. In certain embodiments, the device delivers an agent to the first and/or second microchannel. In certain embodiments, the device delivering the agent can be an automated machine. In certain embodiments, the agent can be more dilute the deeper it moves into the microchannel. In certain embodiments, the agent can be delivered at the concentration and intermittent schedule.

In certain embodiments, the device can deliver the agent to the microchannel(s) through a port (e.g., FIG. 2 (e.g., 212 and/or 222)) in the channel slab, wherein the first opening of the port (e.g., 212 and/or 222) can be to the outside of the body and the second opening of the port (e.g., 212 and/or 222) can be to at least one microchannel. In certain embodiments, a recirculatory flow loop can be used to deliver the agent.

In certain embodiments, the agents can be small molecules, hormones, proteins, or peptides. In certain embodiments, the device delivers the agent to the first microchannel and/or second microchannel. In certain embodiments, the agent can be inflammatory mediators such as, but not limited to, cytokines, growth factors, hormones (e.g., IFNg, LPS, IL-4, IL-13—molecules that promote differentiation of M1 or M2 macrophages). One of ordinary skill in the art would understand to select the appropriate agent(s) for the specific disease process being addressed in the model.

In certain embodiments, the agent induces the disease state of the organ model. For example, agents such as, but not limited to, peptides and growth factors known to be unregulated during specific disease conditions (e.g. transforming growth factor-beta, sonic hedgehog (SHH), connective tissue growth factor, and any other agent released by damaged tissue cells during organ injury that promotes fibrosis), organ injury causing agents (e.g., smoking), chemical injury (e.g., Bleomycin), or inflammatory mediators such as, but not limited to, cytokines, growth factors, hormones (e.g., IFNg, LPS, IL-4, IL-13, M2 macrophages) can be used to induce organ injury (e.g., fibrosis). In certain embodiments, the agent causes oxidative stress.

In certain embodiments, the active agent is used to inhibit or prevent the organ injury. For example, the agent can be a pharmaceutical compound such as PP2 (a specific inhibitor of integrin-associated SRC-kinase signaling) or endogenous inhibitors of fibrosis in vivo such as retinoic acid, Vitamin A, and ATRA. In another example, the agent can be Prostaglandin PGE2. In another example, the agent can be integrin inhibitors. In another example, the agent can be FAK inhibitors. In another example, the agent can be SRC-kinase inhibitors. In another example, the agent can be any type of RTK inhibitor. In another example, the agent can be Rho-GTPase inhibitors. In certain embodiments, any agent identified by one skilled in the art that is known to modulate disease-related signaling pathways can be used for testing.

In certain embodiments, the biomimetic organ model optimizes air-liquid interface culture. In certain embodiments, the first microchannel can have air or gases flowing through the microchannel.

In certain embodiments, the substance of interest can be, for example but not limited to cigarette smoke, nicotine aerosol (e.g., e-cigarets, nicotine vapor), wood smoke, natural plant smoke, silica dust, acrylic dust, celestial dust, particulates, asbestos fibers, solvents, grain dust, engineered nanomaterials, ultrafine particles, pathogenic species (e.g., viruses and bacteria), stem cells, dry powder drugs, aerosolized drugs, bird droppings, and animal droppings.

Referring to the lung for the purpose of illustration and not limitation, the device delivers the agent to the first microchannel. In certain embodiments, the method can include simulating physiological flow conditions. In certain embodiments, the method can include simulating physiological breathing/inhalation conditions. In certain embodiments, the device delivering the agent can be an automatic agent delivering machine. In certain embodiments, the agent can be delivered to the first microchannel such that the distribution of the agent mimics exposure conditions experience by cell linings in the human lung. In certain embodiments, the agent can be more dilute the deeper it moves into the first microchannel. The dilution can be finely tuned and matched to predicted or measured values from smoke or particulates in human in vivo lungs.

In certain embodiments, for the airborne agent delivery (e.g. smoke), the airborne agent can be pulled through the biomimetic organ model. In certain embodiments, there can be a mixing chamber in the apparatus (e.g., the smoke is generated and diluted/humified in a positive pressure flow process, it then fills an open mixing vessel) from which the airborne agent/air mixture can be pulled through the biomimetic organ model at a set flow rate via syringe pump.

In certain embodiments, the culture medium is not delivered to the biomimetic organ model while the agent is being delivered. In certain embodiments, the culture medium is delivered to one microchannel while the agent is delivered to the other microchannel. In certain embodiments, a recirculatory flow loop can be used to deliver the agent.

Figure 8:
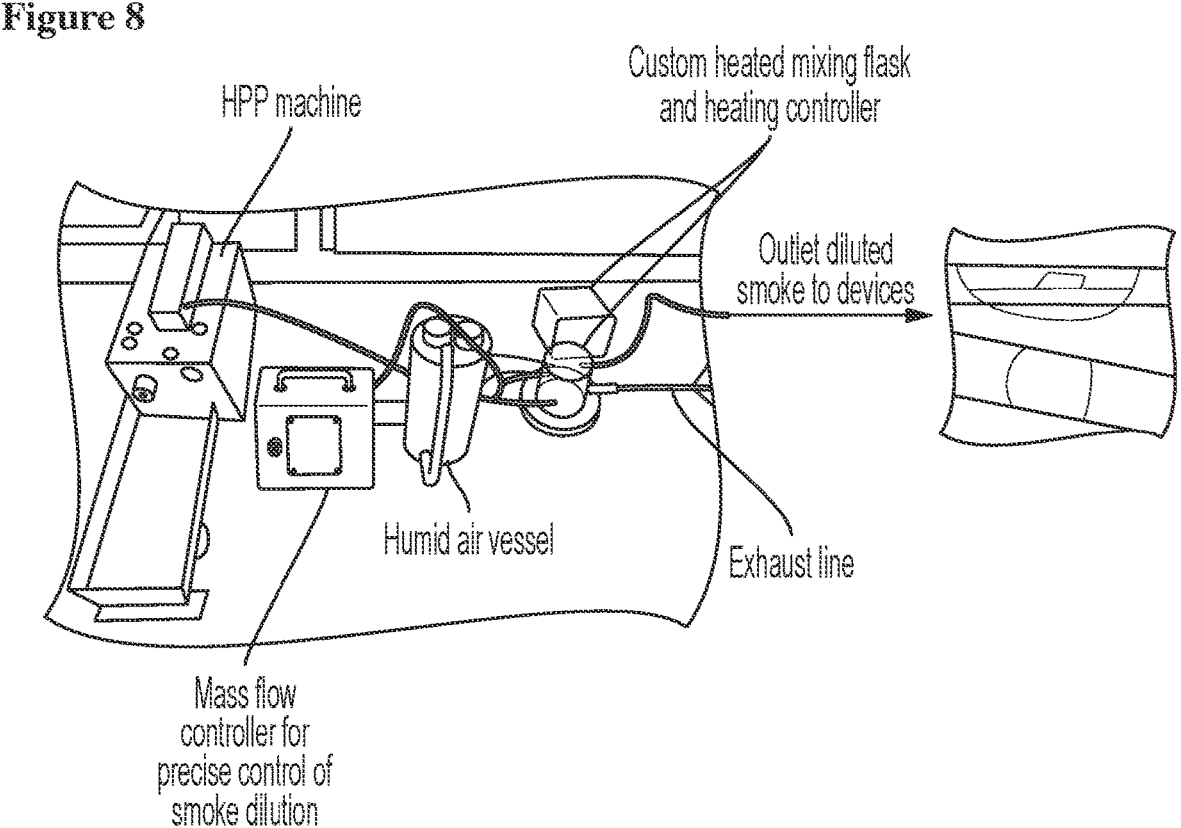
FIG. 8 depicts the use of a gel immobilization technique in connection with sonic hedgehog-driven (SHH) fibrosis, including sonic hedgehog, a pro-fibrotic signaling protein.

In certain embodiments, the device delivering the agent can be an automatic smoking machine (e.g. FIG. 8). In certain embodiments, such a device can be used for any volatile species and/or particulate in addition to tobacco smoke. For example, but not limited to, the automatic machine could be a benchtop-sized, automated smoking machine interfaced with microfluidic devices (e.g., a Human Puff Profile model cigarette smoking machine (CH Technologies)). In certain embodiments, the device can be configured to delivery virtually any chemical and/or particulate species (e.g., electronic cigarette vapor, wood smoke, particulate toxicants, etc.) that can be nebulized/aerosolized such that it can be mixed with humidified air in the same manner as tobacco smoke. In certain embodiments, the Weibel model can be used to estimate appropriate concentration ranges prior to delivery of the agent. In certain embodiments, the agent can be intermittently delivered to model the frequency in which a human's lungs may experience the agent (e.g., to model a heavy versus light smoker). In certain embodiments, the concentration of the smoke mimics that of a lung exposed to secondhand smoke.

In certain embodiments, agents can be delivered to serially connected devices lined with different types of epithelial cells (e.g., nasal, tracheal, bronchial, bronchiolar, and alveolar). In this respect, the model is able to simulate delivery through the entire organ system. Referring to the lung for the purpose of illustration and not limitation, the respiratory tract could be modeled by serially connecting devices to administer an agent to a model of the nose, to a model of the trachea, to a model of the large airways, to a model of the small airways, and finally to a model of the alveoli.

Methods of Use

Figure 7:
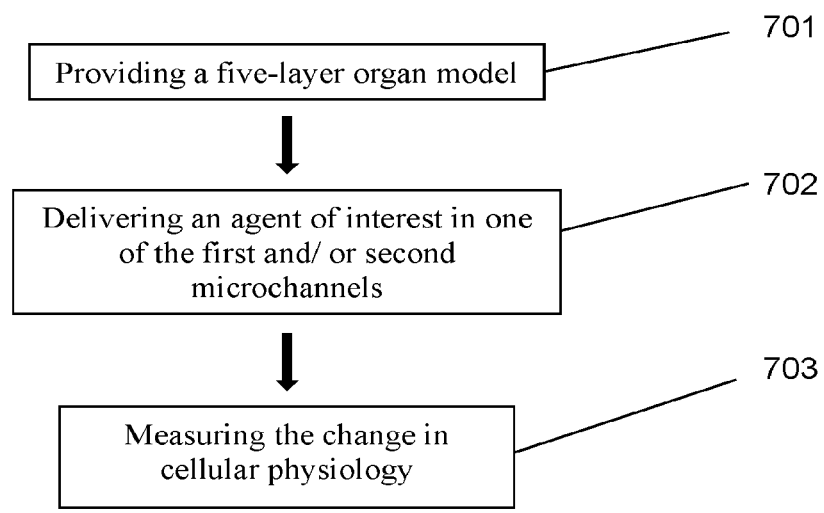
FIG. 7 depicts a schematic representation of an exemplary method according to the disclosed subject matter.

Referring to FIG. 7 for the purpose of illustration and not limitation, an exemplary method of testing the regulation of fibrotic tissue (700) is provided. In certain embodiments, the method can include providing a biomimetic five-layer model (701) as disclosed herein, and can include delivering an agent of interest in one of the first and/or second microchannels (702). In certain embodiments, the method can include measuring a change in cellular physiology (703).

In certain embodiments, the first channel slab, second channel slab, and chamber slab can be separated and each cell compartment (e.g., layer or matrix) can be examined separately. Once each slab is separated, each of the cell compartments can be separately fixed, stained, and/or examined by microscopy. The cells can also be subjected to lysis buffers for the purpose of isolating proteins or nucleic acids or performing biochemical and molecular biological analyses.

In certain embodiments, the method can include measuring pathological responses to the agent. In certain embodiments, the method can include measuring tissue hardening or softening in response to the agent. In certain embodiments, the method can include measuring changes in the viscoelastic properties of the tissue in response to the agent. In certain embodiments, the method can include measuring extracellular matrix reorganization of the tissue in response to the agent. In certain embodiments, the method can include measuring inflammatory and other adverse biological responses, for example, but not limited to, production of cytokines/chemokines and expression of adhesion molecules; production of enzymes (e.g., MMPs, TIMPs, LDH); activation of oxidative stress pathways; production of free radicals; activation of pro-inflammatory pathways; endoplasmic reticulum (protein production) stress; production of extracellular matrix proteins; cell proliferation; gene expression changes; DNA damage; or cell apoptosis and necrosis (e.g., death).

In certain embodiments, the method can include measuring inflammatory responses, for example, but not limited to, production of cytokines/chemokines & expression of adhesion molecules; activation of oxidative stress pathways, endoplasmic reticulum (protein production) stress; DNA damage; or cell apoptosis (i.e., death).

In certain embodiments, the models of the instant disclosure, including but not limited to the five-layer model, can be used to examine fibrosis. In certain embodiments, the gel layer is attached to the chamber as described above. For example, as conditions become profibrotic the gel will eventually detach from a corner or wall of the chamber due to contractile force generated by the cells within the gel layer. In certain embodiments, the collagen-anchored PDMS chamber can extend the time scale before contraction occurs. This can allow for greater sensitivity of examining a treatment (e.g., drug treatment). In certain embodiments, the culture conditions will affect how much the cells try to contract the gel, but it will not affect the method of anchoring the gel. The culture conditions influence the behavior of the cells and will vary from conditions that promote low contractility to pro-fibrotic conditions with high contractility. The latter would be achieved by a myriad of growth factors, increased serum concentration or using an injury model (induced via a cellular response). In certain embodiments, the culture conditions could be varied but not impact the physical anchoring. In certain embodiments, the platform can model a fibrotic organ model. In certain embodiments, the biomimetic fibrotic organ model, an agent can induce or inhibit fibrosis.

In certain embodiments, the biomimetic organ models of the instant disclosure can include additional elements, including additional membrane layers, for example but not limited to, integrated pumps, valves, bubble traps, oxygenators, gas-exchangers, in-line microanalytical functions, and other suitable elements. Such elements can allow for additional control and experimentation using the biomimetic organ model. In certain embodiments, the biomimetic organ model can include features for automatically performing experiments on the biomimetic organ model. For example, in some embodiments, the gel layer can incorporate magnetic materials, exothermic or endothermic materials, light emitting or absorbing materials, mechanically actuatable materials, electrically actuatable materials, or combinations thereof. For example, in some embodiments, the biomimetic organ model can include automated valves, pumps, or fluid (e.g., liquid, gas, or emulsions) control mechanisms or automatic monitoring and testing mechanisms, such as sensors, detectors, or monitors. In certain embodiments, the biomimetic organ model can be configured to be coupled with other sensors, detectors, or monitors not disclosed on the biomimetic organ model. In certain embodiments, the biomimetic organ model can be configured to be coupled with other bioanalytical platforms and methodologies (e.g., gel electrophoresis, capillary electrophoresis, western blotting, ELISA, mass-spectrometry) not disclosed on the biomimetic organ model. In certain embodiments, the biomimetic organ model can include a cleaning reservoir coupled to the channels for cleaning or sterilizing the channels. In certain embodiments, the biomimetic organ model can be modular in construction, thereby allowing various elements to be attached or unattached as necessary during various cleaning, experimenting, and imaging processes. In certain embodiments, the biomimetic organ model, or portions thereof, can be reusable, and in some embodiments, the biomimetic organ model, or portions thereof, can be disposable.

The following examples are offered to more fully illustrate the invention, but are not to be construed as limiting the scope thereof.

EXAMPLES

Example 1

Five-Layer Organ Model

The first and second channel slabs and the chamber slab of the model were formed using soft lithography techniques, in which the PDMS mixture was poured over the mold, and the slabs were allowed to cure. The microchannels were etched into each of the channel slabs, with the dimensions of 10 mm×1 mm×0.15 mm (length×width×height). The chamber was etched into the chamber slab, with the dimensions of 6 mm×3 mm×1 mm (length×width×height). See FIG. 9 for a picture of the five-layer model and FIG. 2A-2B for a schematic of the five-layer model.

Figure 9:
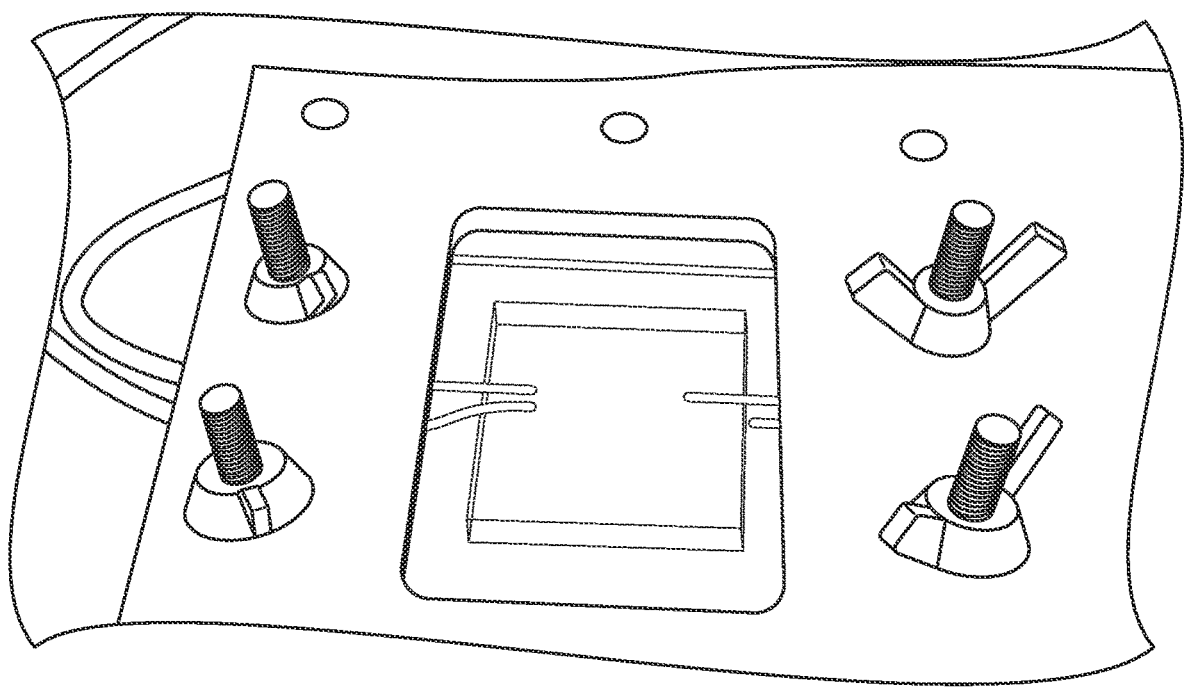
FIG. 9 depicts an exemplary clamp apparatus for mechanically bonding the different layers of the biomimetic organ model together.
Figure 10:
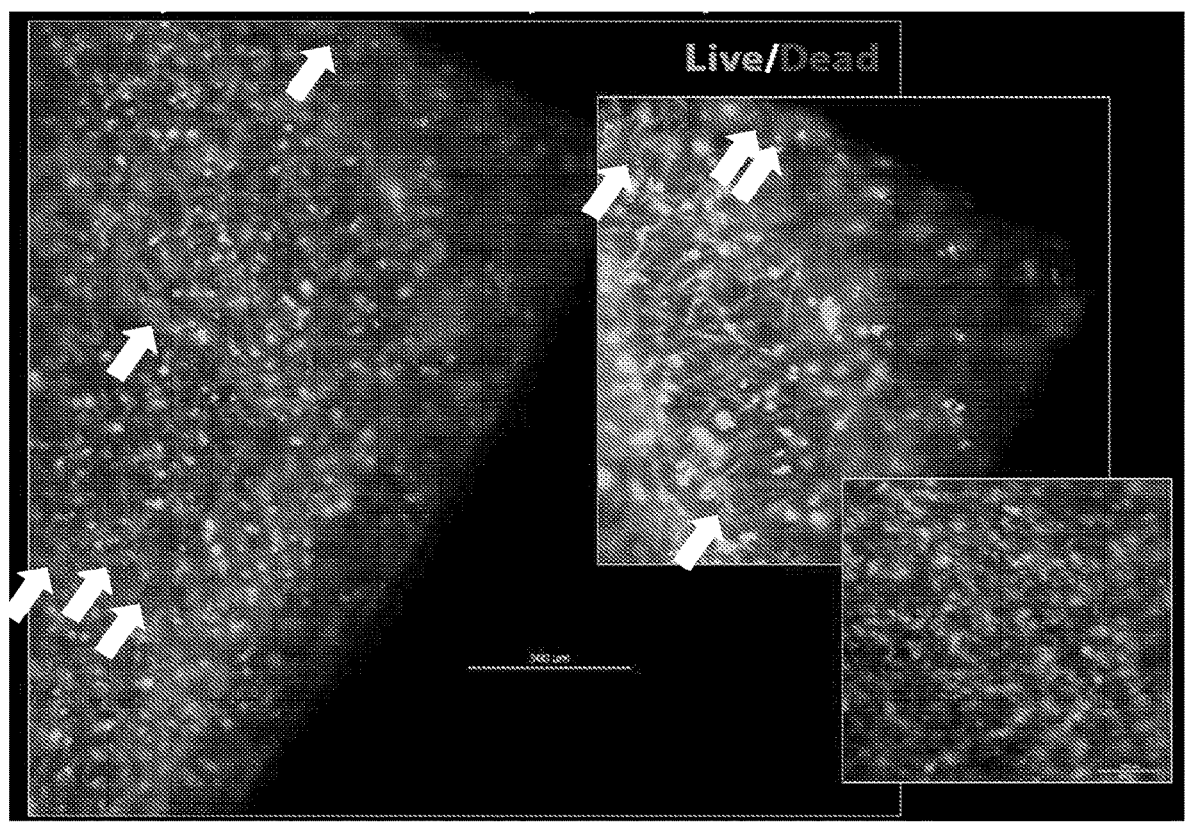
FIG. 10 depicts the cellular physiology of the stromal cells after 5 days in culture. The arrows denote dead cells.

In order to test whether the cells in the gel layer can be fed via the channels, experiments were conducted with only cells in the gel layer (example shown in FIG. 10). In particular, human lung fibroblasts and THP-1 cells, a human macrophage-like cell line, were included in the gel layer. The gel was created by adding collagen to physiological aqueous buffer. Additionally, or alternatively, any process yielding a collagen-based hydrogel may be used. The collagen solution to be used in gel preparation can typically be in, but is not limited to, the concentration range of 0.1 to 10 mg/ml of collagen. Human lung fibroblasts (100 K cells/ml) and THP-1 macrophage (50 K cells/ml) cells were added to the gel during the liquid phase (e.g., collagen solution at 4° C.). The side of the membranes facing the chamber slab (e.g. 242 and 251) were treated with sulfo-sanpah to promote collagen/ECM anchorage. The lower channel slab, lower membrane, and chamber slab were stacked. The gel was then pipetted into the chamber (e.g., 231). After the upper membrane and upper channel slab was placed on top, the biomimetic organ model was clamped and the biomimetic organ model was placed in the incubator at 37° C. A picture of the clamp apparatus is shown in FIG. 9. The biomimetic organ model was incubated for five days. For continuous perfusion of culture medium at 200 μL/hr in each channel, FGM-2 can be used as the medium having a reduced serum (e.g., between 0-2% and 2%). The stromal cells in the gel layer of the five-layer model exhibited greater than 99% viability (FIG. 10). Thus, it was demonstrated that the cells in the gel layer can be fed via the channels in the full five-layer assembly.

Figure 11:
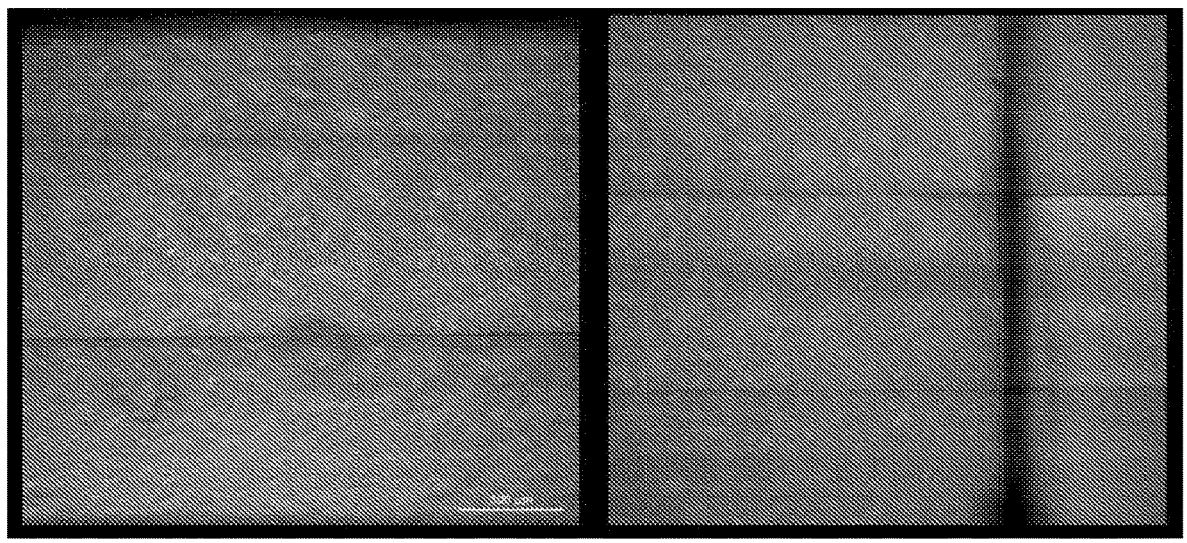
FIG. 11 depicts one embodiment of the cellular physiology of the cell-lined fluidic channels with the gel layer of the 5-layer model.

Next, the cellular physiology of the cell-lined fluidic channels with the gel layer of the five-layer model was examined (FIG. 11). In this instance, the upper channel contained human lung endothelial cells cultured with commercially available medium from the supplying vendor of the cells. The lower channel contained small airway epithelial cells with similar specific medium, both from same vendor. The gel was created by adding collagen to physiological aqueous buffer at a concentration of 2 mg/ml and kept at 4° C. Human lung fibroblasts (100 K cells/ml) were added to the gel during the liquid phase. The side of the membranes facing the chamber slab were treated with sulfo-sanpah to promote collagen/ECM anchorage. The lower channel slab, lower membrane, and chamber slab were stacked. The gel was then pipetted into the chamber. After the upper membrane and upper channel slab was placed on top, the biomimetic organ model was clamped. The endothelial and epithelial cells were then introduced via injection into the channel after presoaking with medium and ECM coating. FIG. 11 is a phase contrast image, taking during the culture period, depicting the interface between the gel and two membranes. The culture period, in this example, was 1 week. However, the culture period can have a longer duration (e.g., several weeks).

Example 2

Five-Layer Lung Fibrosis Model

This example presents a microengineered modular platform that leverages three-dimensional cell culture in a compartmentalized microdevice to replicate organ-specific alterations in the cellular composition, soluble microenvironment, tissue microarchitecture and local changes in the mechanical properties of stromal tissue during fibrosis. This system combines tissue-engineered hydrogel constructs impregnated with human fibroblasts with perfusable microchannels to mimic the stromal-vascular and stromal-epithelial interface.

The ability to tune fibrotic responses using this model was demonstrated by varying the microenvironment to form a normal stroma consisting of quiescent human lung fibroblasts (HLFs) or to induce the development of fibrotic foci comprised of proliferating HLFs and a dense ECM. Furthermore, this example demonstrated the potential of this system for therapeutic screening by showing attenuated fibrotic responses via inhibition of integrin-mediated signaling known to promote organ fibrosis in vivo.

The first and second channel slabs and the chamber slab of the model was formed using soft lithography techniques, in which the PDMS mixture was poured over the mold, and the slabs were allowed to cure. The microchannels were etched into each of the channel slabs, with the dimensions of 10 mm×1 mm×0.15 mm (length×width×height). The chamber was etched into the chamber slab, with the dimensions of 6 mm×3 mm×1 mm (length×width×height).

Figure 12:
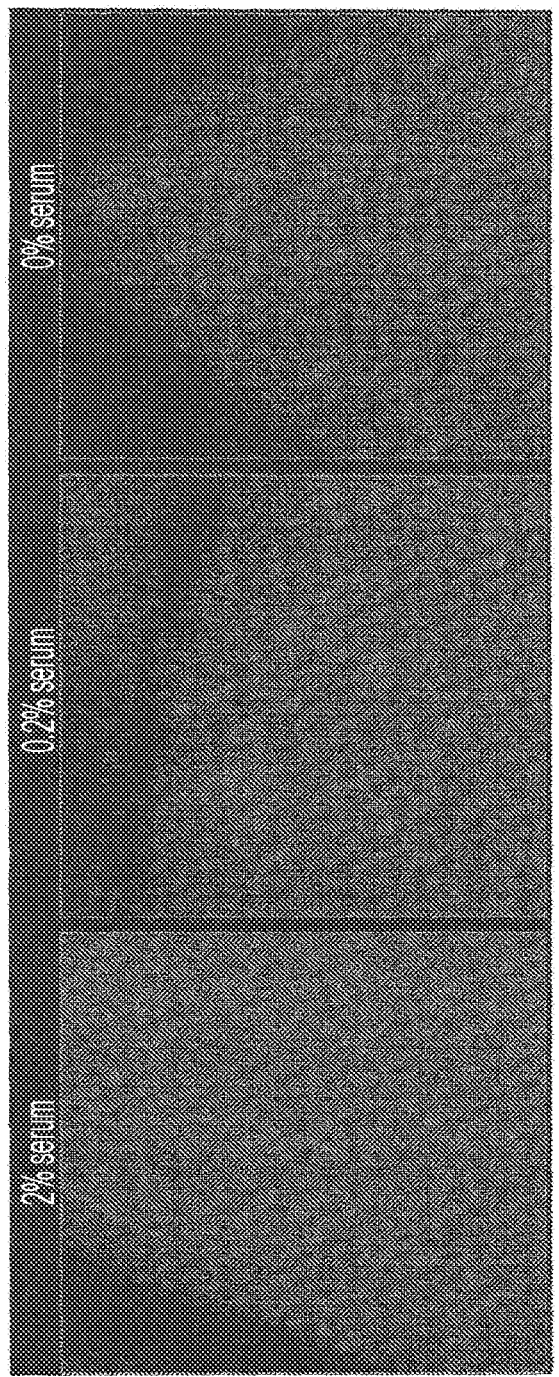
FIG. 12 depicts the effect of serum concentrations on cell viability and density.
Figure 13:
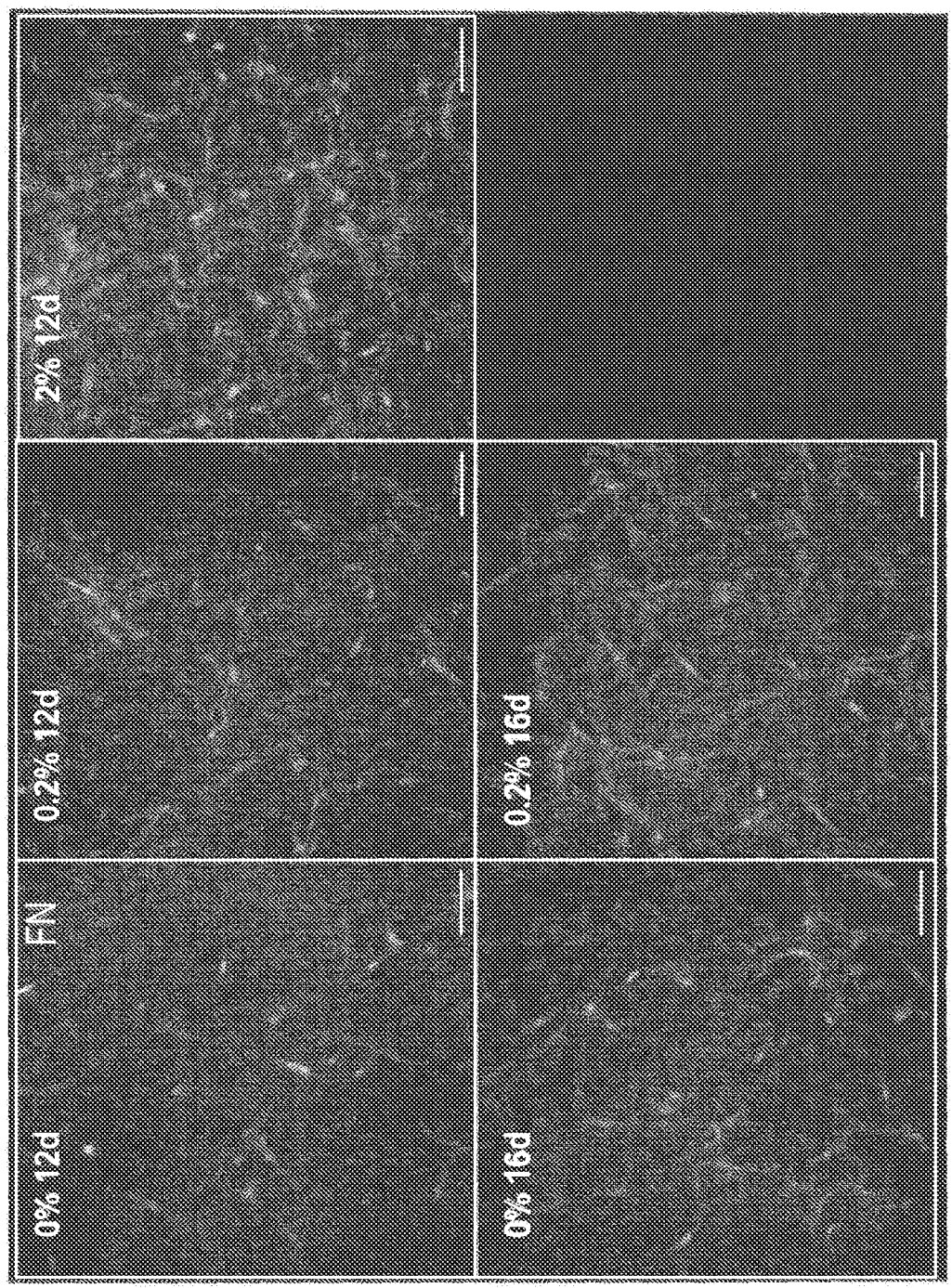
FIG. 13 depicts fibroblast proliferation induced by varying the serum concentration and culturing for 12 days or 16 days via staining of fibronectin (FN) and smooth muscle actin (SMA).
Figure 14:
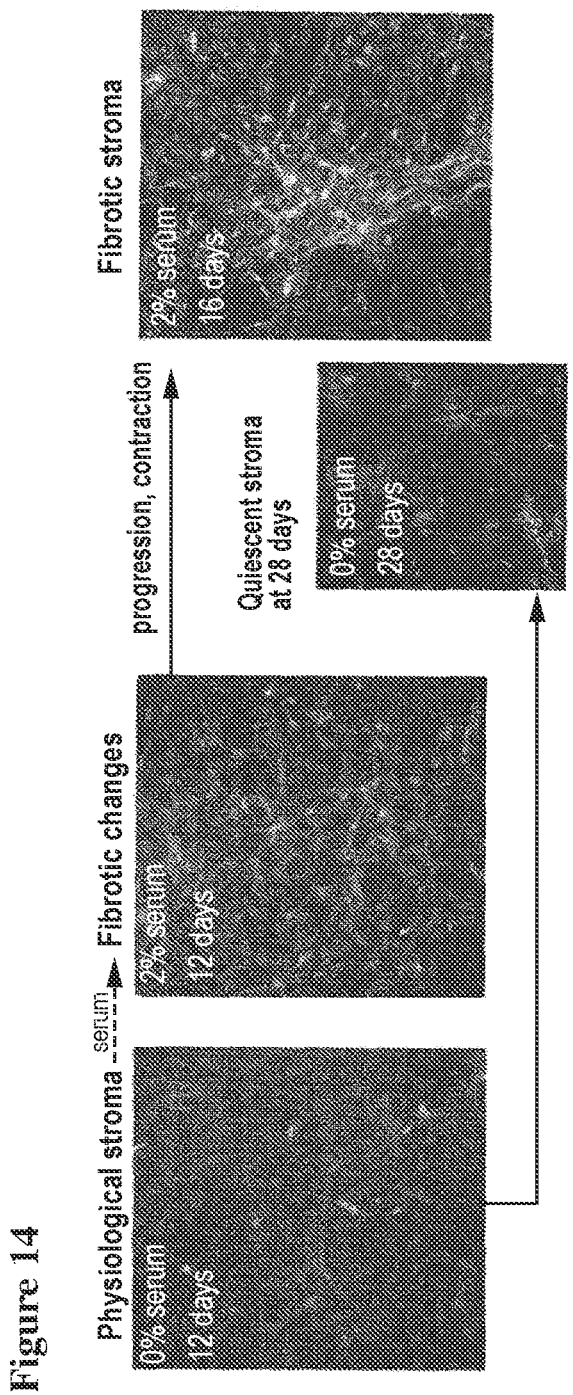
FIG. 14 depicts fibroblast proliferation induced by varying the serum concentration and culturing for 12, 16, or 28 days via staining of fibronectin (FN) and smooth muscle actin (SMA).
Figure 15:
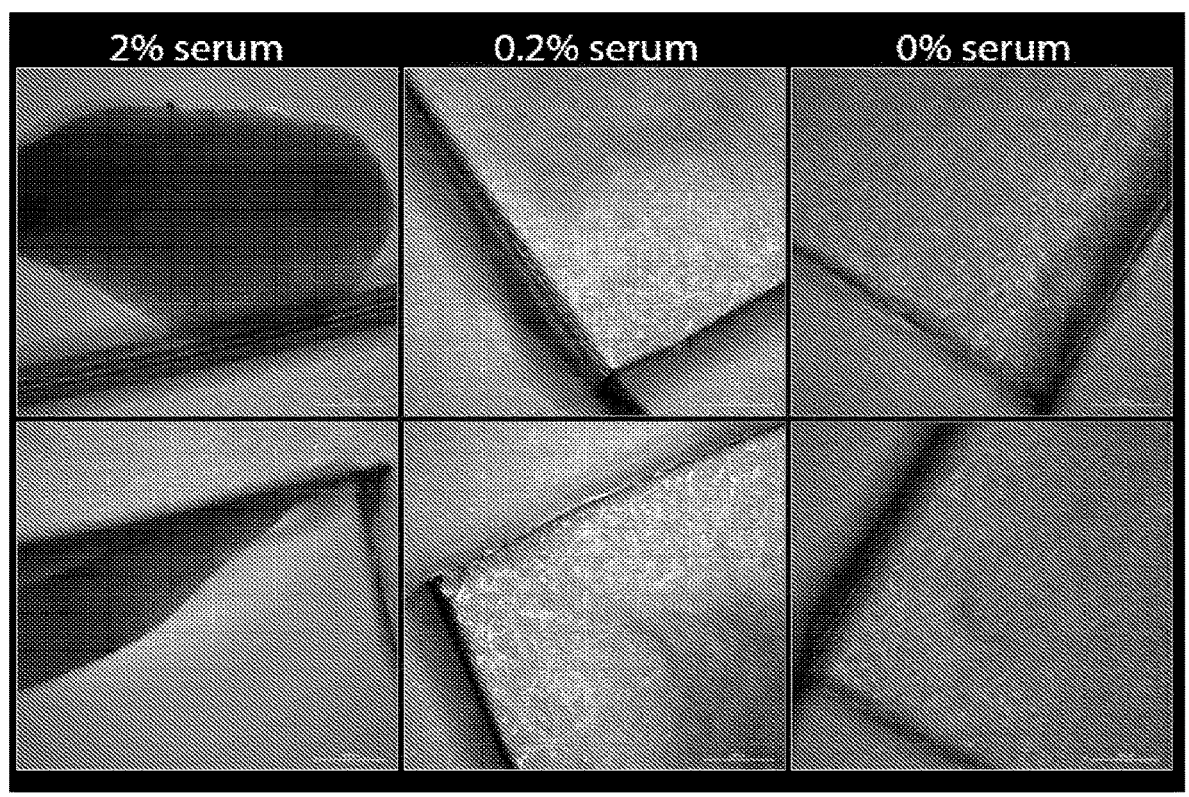
FIG. 15 depicts detachment of the gel layer from the chamber induced by varying the serum concentration and culturing for 16 days.
Figure 16:
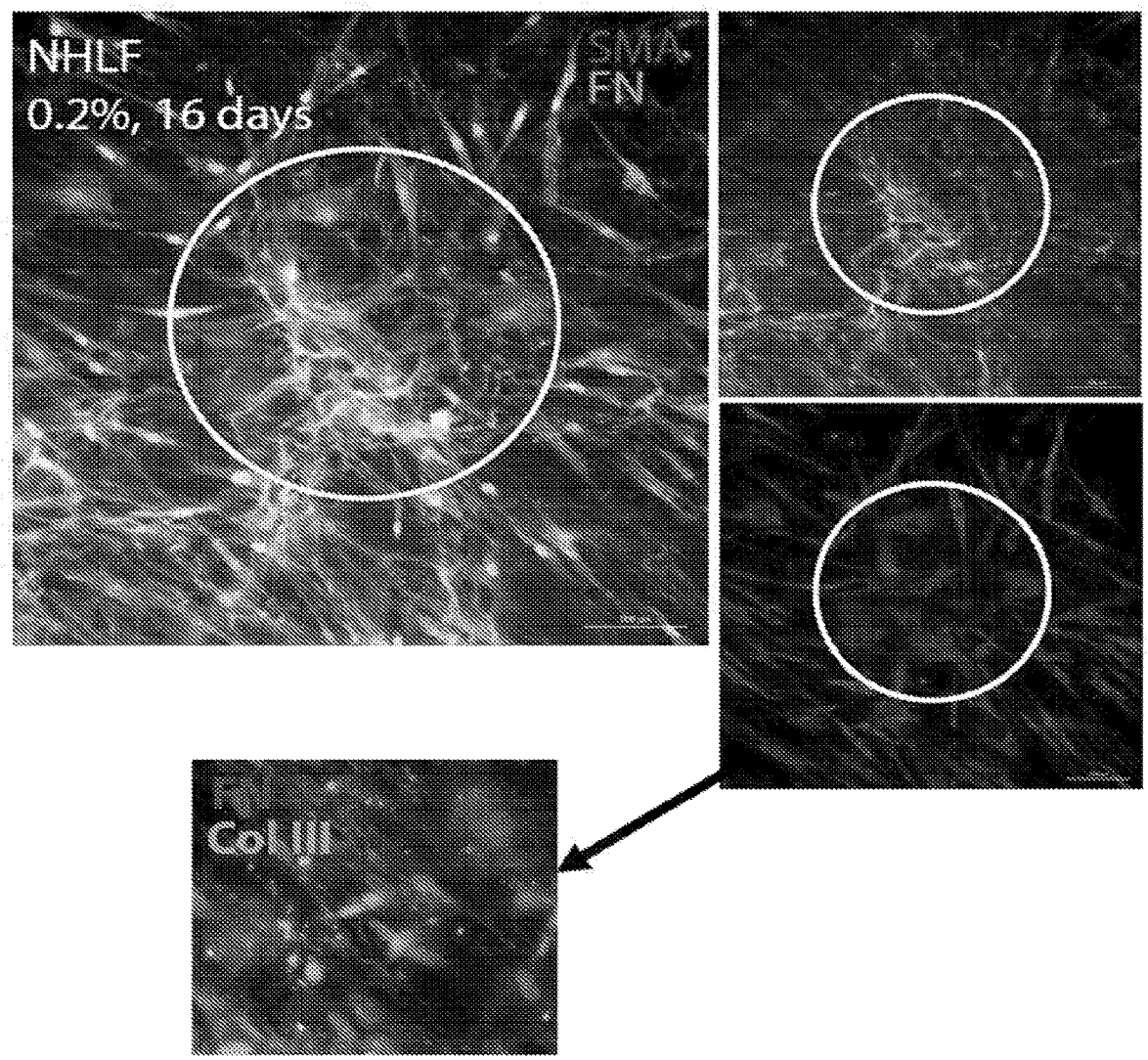
FIG. 16 depicts distinct stromal cell subsets and emergent fibrotic foci following culturing the gel layer in 0.2% serum for 16 days.

In the first series of validation experiments, fibrotic responses of stromal cells embedded in the gel layer were induced by varying the serum concentration in the culture media. Incubating the gel layer containing the NHLF cells for 12 days in 2% serum lead to increased cellular density indicative of fibrotic change, as indicated by live/dead staining (FIG. 12). Incubating the gel layer containing the NHLF cells in 2% serum lead to cellular proliferation indicative of a fibrotic response, as the cells are very dense relatively and the gel has detached and begun to contract and fold over. By day 16, treatment with 0.2% serum lead to fibrotic changes and treatment with 2% serum lead to fibrotic stroma (FIGS. 13 and 14; stained for fibronectin (FN) and smooth muscle actin (SMA)). Changes with the 0.2% at day 16 were minor in comparison to 2% serum but more fibrotic than 0% serum. These results demonstrate the ability to visualize and measure subtle variations in organ-specific fibrotic responses. Detachment of the gel layer from the chamber was observed in most constructs cultured with 2% serum for 16 days (FIG. 15). Fibrotic foci-like structures with dense fibronectin matrix and collections of polygonal cells (indicative of pathological myofibroblast differentiation) appeared in constructs cultured with 0.2% serum for 16 days (FIG. 16; stained for FN and SMA).

Figure 17:
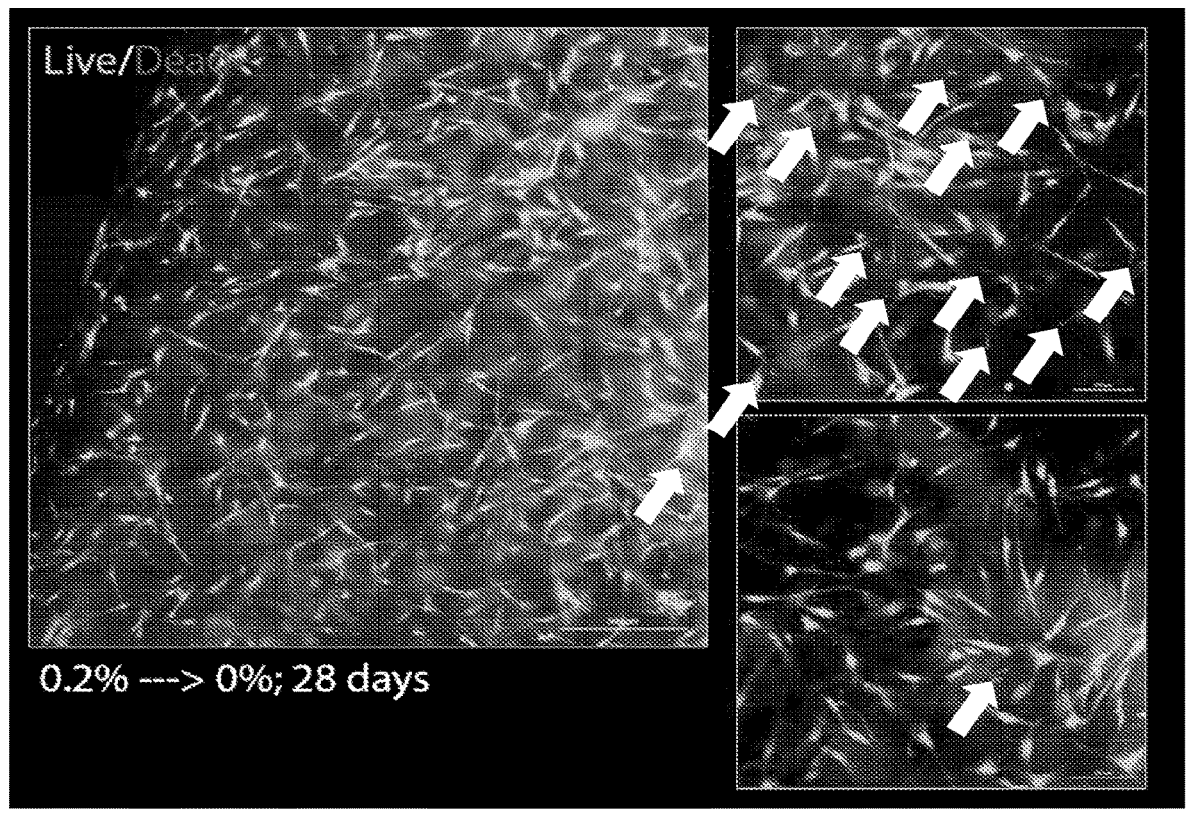
FIG. 17 depicts live/dead staining after long periods of culture. The arrows denote the few dead cells.

When the serum concentration was reduced from 0.2% to 0%, after 28 days the cells were quiescent and no contraction of the gel layer occurred (FIG. 17; arrows denote the few dead cells). Here, the cells were cultured in 0.2% in a 2D culture prior to use in the 3D model to promote lower levels of proliferation and ensure a more quiescent phenotype in 3D culture. The cells are normally grown in 2% serum but in this experiment they were cultured in 0.2% serum to slow down their rate of growth. They were placed in 0% serum concentration in the model, and they stay at 0% serum for up to 28 days as shown in figure with high viability. The live/dead staining in FIG. 17 demonstrated quiescence based on low cell density after a long period of culture.

Figure 18:
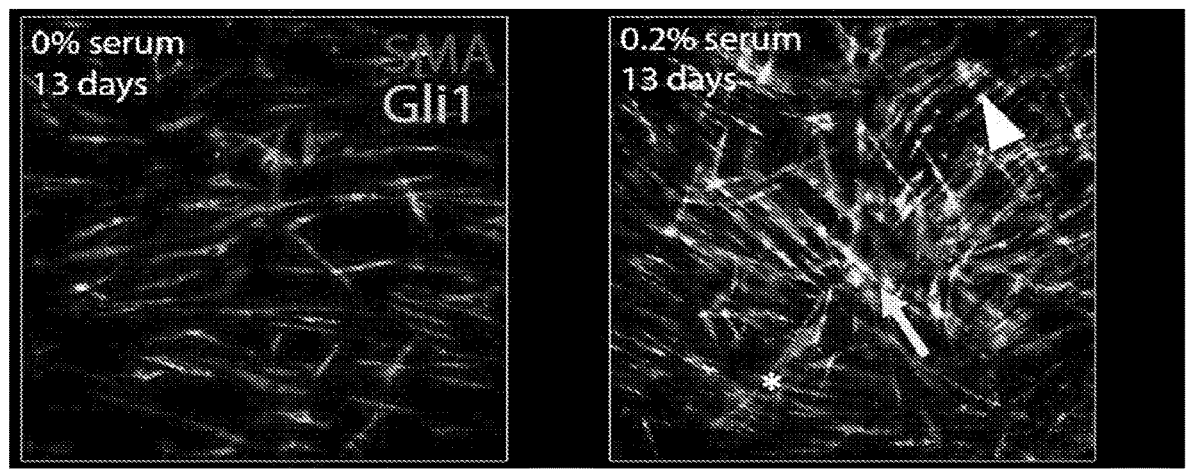
FIG. 18 depicts the presence of Gli-1 in the stromal layer of the five-layer model.
Figure 18:

The presence of glioblastoma-1 (Gli-1), a marker of myofibroblast cells, present in fibrotic lesions, indicated that this is a valid fibrosis model as activity of Gli-expressing cells is a relevant pathological feature of the in vivo disease (FIG. 18) as shown in Kramman et al., Cell Stem Cell. 16(1):51-66 (2015). In the gold standard model mouse bleomycin model depicted in FIG. 18, the staining pattern observed in the mouse model of lung fibrosis is similar to what is observed in the disclosed engineered human model.

Using different serum concentrations demonstrated the ability to measure increased in fibrotic outputs including cell proliferation, extracellular matrix ECM production, and changes in stromal cell shape in areas of intense ECM production. The 3D nature of the cell culture and preservation of stromal tissue geometry (e.g. preventing contraction and detachment) was important to modeling fibrosis.

Example 3

Five-Layer Injury Model

In this study, the development of the organ injury model was examined. A biomimetic lung model was fabricated as indicated in Example 1.

The serum concentration studies above in Example 2 is one example of tunable fibrosis in the model. In this example, we studied an agent induced injury model. Injured epithelial cells release sonic hedgehog (SHH), so SHH was added exogenously to determine if a fibrotic response can be induced. The initial conditions (e.g., cell density, gel concentration, etc.) did not change from the previous examples (Examples 1 and 2). However, the agent used is different in Example 3 from Examples 1 and 2. For example, SHH was added at 500 ng/ml to produce the pro-fibrotic effect.

Figure 19:
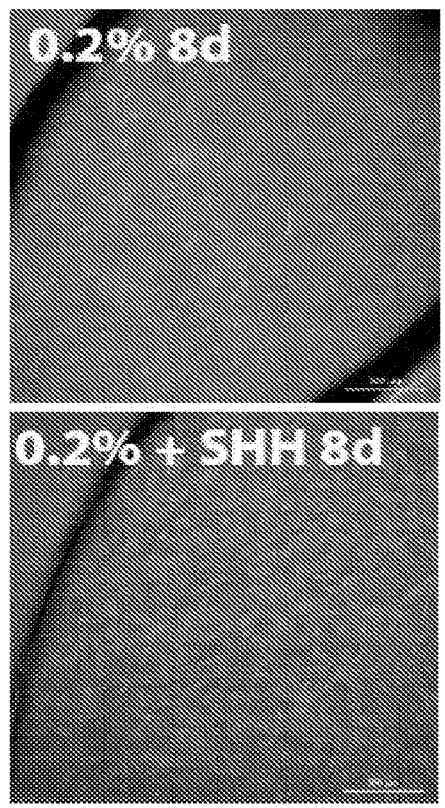
FIG. 19 depicts the use of a gel immobilization technique to study sonic hedgehog-driven (SHH) fibrosis including sonic hedgehog, a pro-fibrotic signaling protein.

As demonstrated in FIG. 19, a fibrotic response can be induced by treating the cells with SHH.

Example 4

Modulation of Fibrotic Disease Processes Using the Biomimetic Five-Layer Lung Fibrosis Model This example examined the regulation of the fibrotic pathway using inhibitors to reduce serum-induced fibrosis. In order to investigate this, PP2 and separately retinoic acid (RA) were added to the cell culture media. PP2 is a non-selective proto-oncogene tyrosine-protein kinase Src (SRC kinase) inhibitor. Src kinases transduce signals that control normal cellular processes such as cell proliferation, adhesion and motility. PP2 is known to promote a deactivated/quiescent state of cultured (myo)fibroblasts by inhibiting activation pathways. These kinases are found on integrin signaling complexes and have been shown to regulate integrin signals. Therefore, blocking SRC kinases effectively blocks integrin signaling intracelluarly without directly interfering with cell adhesion. Retinoic acid is involved in extracellular matrix biosynthesis.

A biomimetic lung model was fabricated as indicated in Example 1.

Figure 20:
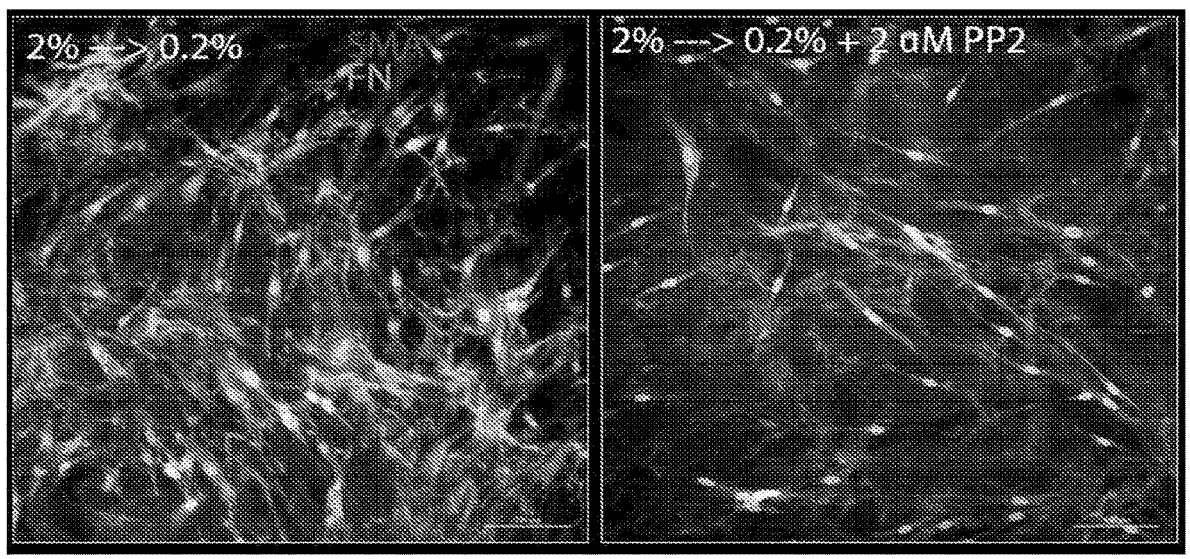
FIG. 20 depicts SRC kinase inhibition induced reduction in serum-induce fibrosis.

The cells for the PP2 study were cultured in 2D with 2% serum and then switched to 0.2% in the model. 2 µM of PP2 was added to the medium 24 hours after assembly of the model and maintained for the duration of the study. PP2 reduced fibrosis, demonstrating this could be used as a screening platform for inhibitors of fibrosis (FIG. 20). The initial conditions (e.g., cell density, gel concentration, etc.) did not change from the previous examples (Examples 1, 2, and 3). However, the agent used is different in Example 3 from Examples 1 and 2.

Figure 21:
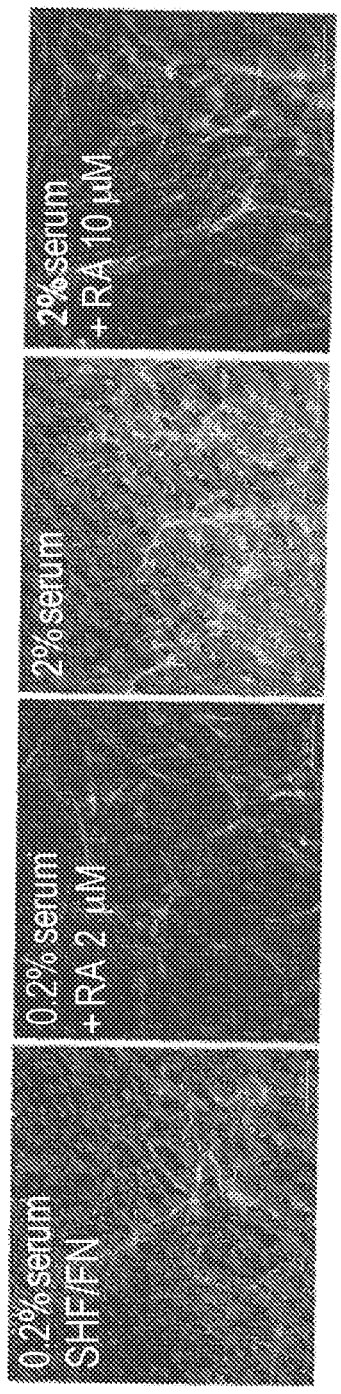
FIG. 21 depicts retinoic acid induced reduction in serum-induce fibrosis.

For retinoic acid treatment, the cells and densities were the same as indicated for FIG. 11 of Example 1. The cells were cultured in 0.2 or 2% serum with or without 2 µM RA (0.2% serum) or 10 µM RA (2% serum), following similar steps as the previous examples (e.g., Examples 1-3). FIG. 21 depicts the RA inhibited serum-induced fibrotic response.

Example 5

Modeling Injury Induced Fibrosis Using the Biomimetic Five-Layer Lung Fibrosis Model Typically organ fibrosis occurs secondarily to an organ injury. A critical aspect of modeling related inflammatory and fibrotic disease processes absent in current state-of-the-art models of tissue fibrosis is the incorporation of resident immune cells, such as macrophages, which are present in the stroma at the location of organ injury and play a key role in mediating the organ injury response, which when pathologically altered entails fibrotic progression. Gel anchorage and incorporation of resident immune cells are differentiating characteristics compared to other platforms such as the so-called "Scar in a jar" platform. The biomimetic five-layer lung fibrosis model was used to examine injury induced fibrosis, including macrophage differentiation.

A biomimetic lung model was fabricated as indicated in Example 1, and the cells were plated and cultured as indicated for FIG. 11. Primary monocytes derived from healthy human donors were used instead of THP-1 cells (e.g., a cell line derived from leukemia). As illustrated by this experiment, engineered stromal microenvironment can permit and/or promote differentiation of human blood monocytes into tissue macrophage cells.

Figure 22:
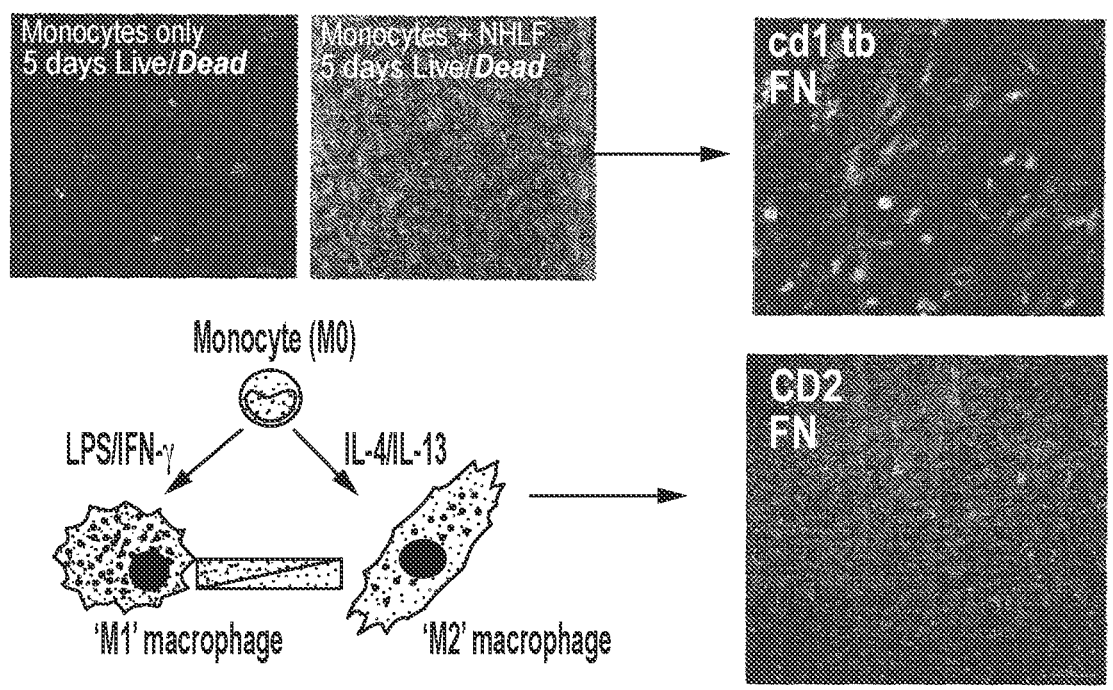
FIG. 22 depicts the presence of CD11b and CD206 in the stromal layer of the five-layer model.

In the absence of NHLF, monocytes did not proliferate and were not viable (FIG. 22). After the addition of NHLF and culturing for 7 days without serum, the cells began to differentiate and express CD11b (FIG. 22), which is an integrin complex that the cells use to adhere and migrate through the tissue. Under the same conditions, the cells also began to differentiate and express CD206 (FIG. 22), which is a marker of differentiated tissue macrophages.

Figure 23:
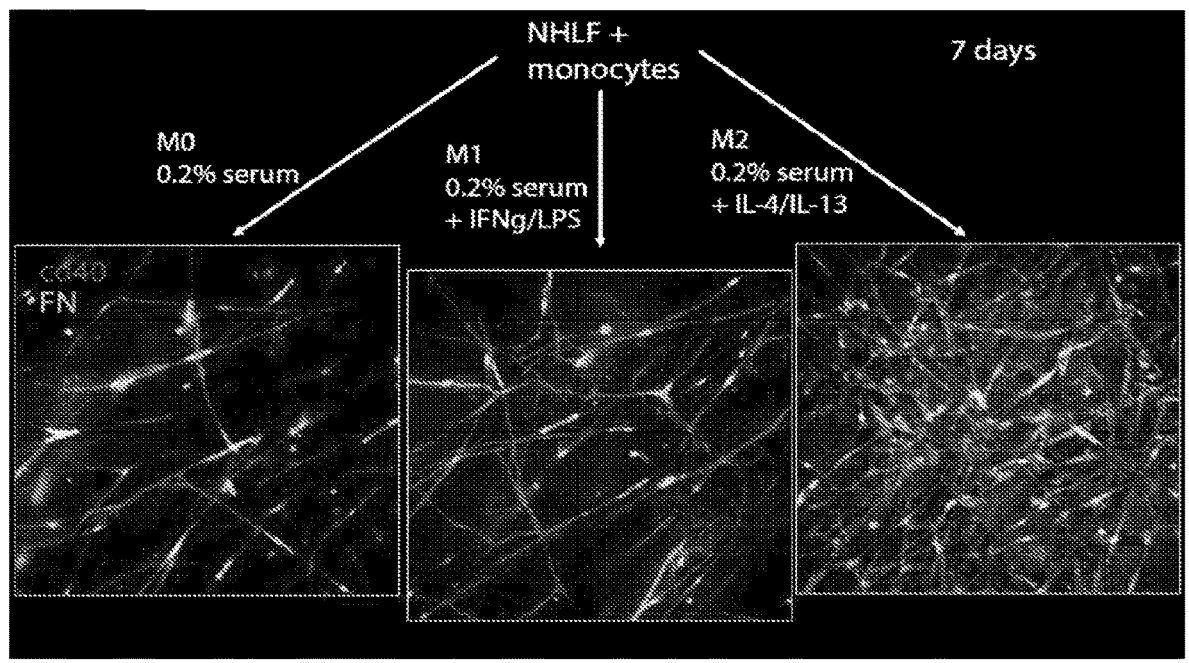
FIG. 23 depicts the effect of M2 microenvironment promotion of fibrosis.
Figure 24:
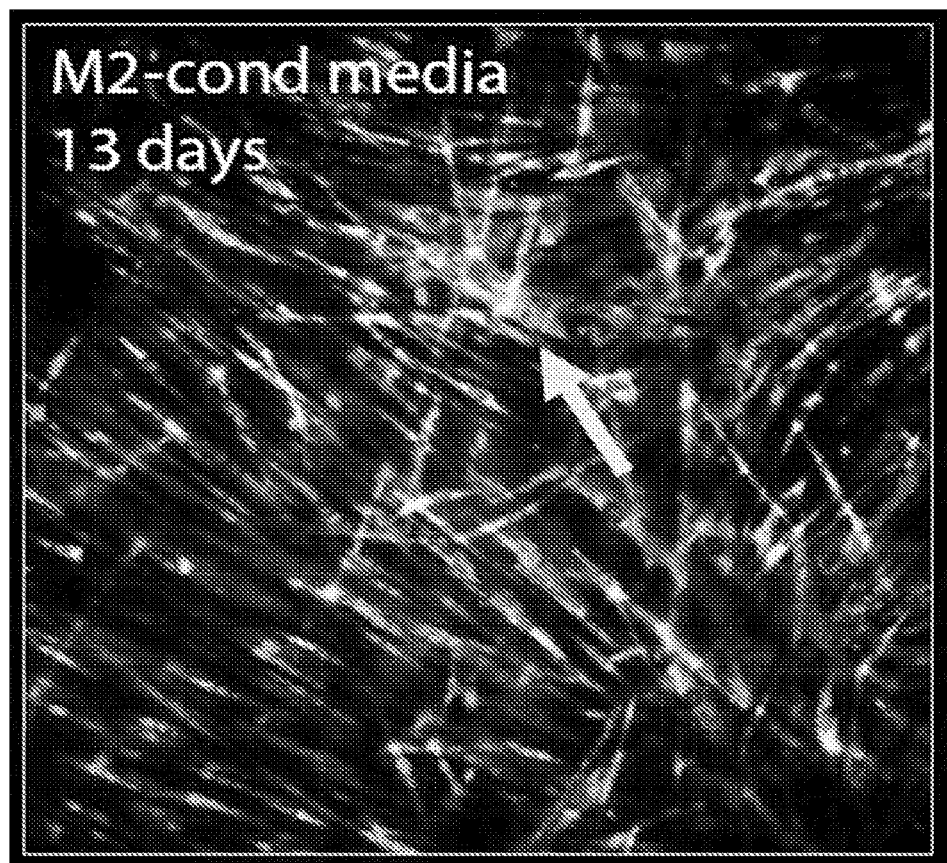
FIG. 24 depicts the presence of Gli-1 in the stromal layer of the five-layer model in M2 conditioned media.
Figure 25:
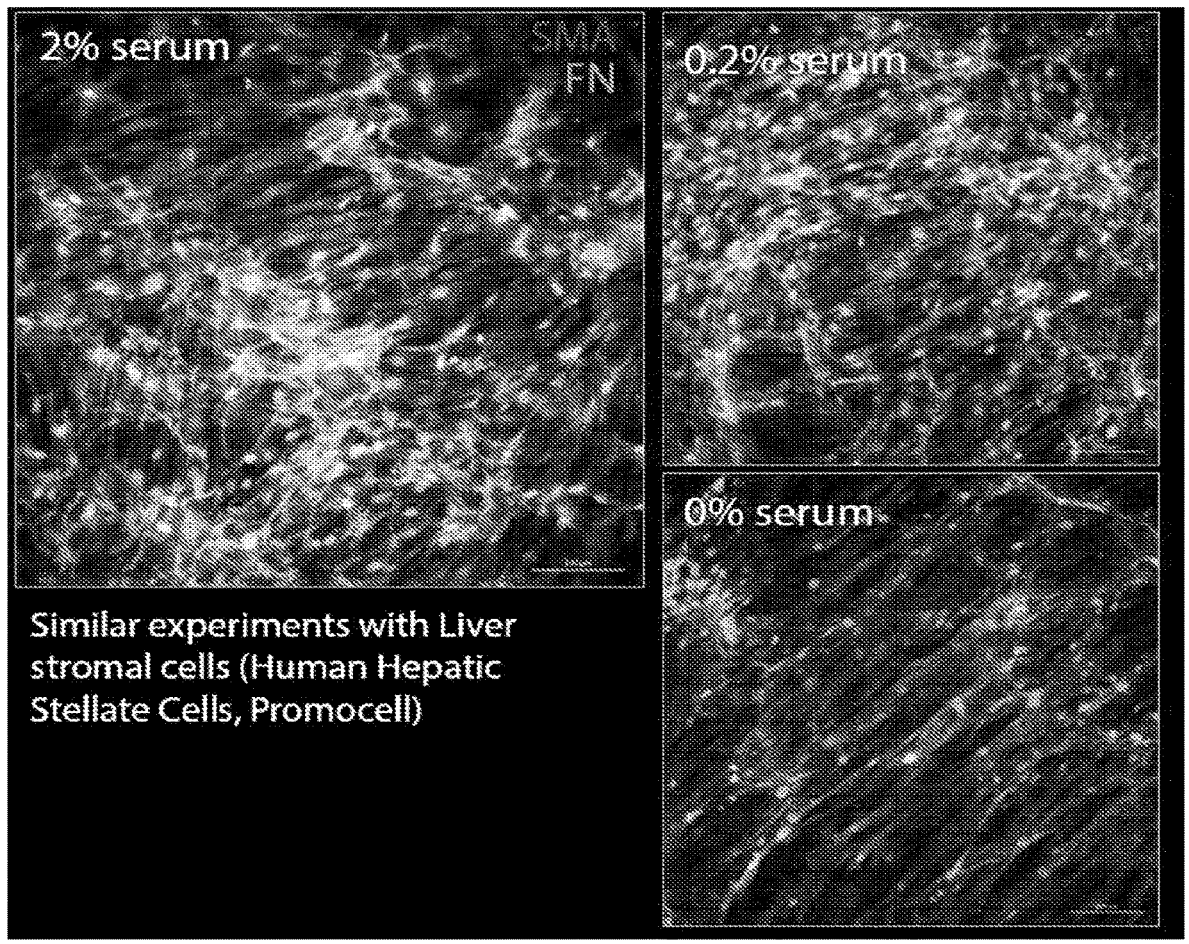
FIG. 25 depicts fibroblast proliferation in a five-layer liver model.

M2 is a phenotype of tissue macrophages, and can be further elevated by IL-4 and produce high levels of IL-10, TGF-beta and low levels of IL-12. M2 macrophages are known to decrease inflammation, and would be present post tissue injury. Culturing the cells in the presence of M2-polarized macrophages promoted fibrosis in the microengineered stromal tissue gel layer, while M1-polarized macrophages did not (FIG. 23). Culturing the cells for 13 days in the M2 conditioned media (contains the natural mixture of factors secreted by M2 macrophases cells) induced the presence of Gli-1 marker of myofibroblast cells (FIG. 24). The arrow indicates a cluster of cells that co-express SMA and Gli-1 at high levels. These would be the cells that are found in fibrotic foci in vivo and serves as a validation of the model compared to what is known from organ fibrosis models in mice.

Example 6

Biomimetic Five-Layer Liver Fibrosis Model

The first and second channel slabs and the chamber slab of the model was formed using soft lithography techniques, in which the PDMS mixture was poured over the mold, and the slabs were allowed to cure. The microchannels were etched into each of the channel slabs, with the dimensions of 10 mm×1 mm×0.15 mm (length×width×height). The chamber was etched into the chamber slab, with the dimensions of 6 mm×3 mm×1 mm (length×width×height).

To realize a liver model, primary human lung fibroblasts were replaced with primary human hepatic stellate cells. The liver-specific stromal cells implicated in hepatic fibrosis. HHSC were acquired from Promocell and maintained in a vendor-supplied culture medium, although any standard fibroblast medium such as FGM-2 with low serum concenrations can also be used as a suitable substitute. To realize further organ-specific embodiments, stromal cells derived from the organ of choice can form the basis of any particular organ-specific fibrosis model.

Increased levels of serum also induced fibrosis in the liver model (FIG. 24).

The present disclosure is well adapted to attain the ends and advantages mentioned as well as those that are inherent therein. The particular embodiments disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above can be altered or modified and all such variations are considered within the scope and spirit of the present disclosure. Various publications, patents and patent application are cited herein, the contents of which are hereby incorporated by reference in their entireties.

The invention claimed is:

1. A multi-layer biomimetic organ model comprising:
at least two channel slabs, at least one microchannel being disposed in each of the at least two channel slabs;
at least one chamber slab having at least one chamber disposed therein, the at least one chamber, exposed at a first surface of the at least one chamber slab and exposed at a second surface of the at least one chamber slab, an internal surface of the at least one chamber, between the first surface and the second surface, being uninterrupted;
at least one membrane disposed between at least one of the at least two channel slabs and the at least one chamber slab, the at least one membrane having a first side facing at least one microchannel of one of the at least two channel slabs and a second side facing the at least one chamber of the at least one chamber slab;
a layer of cells coating at least the first side of the at least one membrane;
a gel layer disposed in the at least one chamber of the at least one chamber slab, the gel layer being configured to be anchored on the internal surface of the at least one chamber of the at least one chamber slab for adjusting contraction time of the gel layer; and
at least one device to deliver at least one agent through one or more of the at least one microchannel, wherein the layer of cells coating the first side of the at least one membrane comprising epithelial cells,
the at least one microchannel disposed in each of the at least two channel slabs are in fluid communication through the at least one membrane and the gel layer disposed in the at least one chamber of the at least one chamber slab.

2. The multi-layer biomimetic organ model of claim 1, wherein the at least two channel slabs and the at least one chamber slab individually comprise glass, metal, alloy, plastic, wood, paper, or a polymer.

3. The multi-layer biomimetic organ model of claim 1, wherein the at least one membrane comprises polyester thin clear fabric, polydimethylsiloxane, polymeric compounds, or natural membranes, the natural membranes comprising collagen, laminin, or a combination thereof.

4. The multi-layer biomimetic organ model of claim 1, wherein one or more of the at least one microchannel disposed in each of the at least two channel slabs has a width from 0.01 nm to 1 cm and a length from 1 mm to 10 mm.

5. The multi-layer biomimetic organ model of claim 1, wherein the gel layer is embedded with tissue or cells.

6. The multi-layer biomimetic organ model of claim 5, wherein the tissue or cells comprise basal stromal tissue or basal stromal cells.

7. The multi-layer biomimetic organ model of claim 1, wherein the gel layer comprises extracellular matrix proteins selected from the group consisting of, collagen, fibronectin, laminin, hyaluronic acid, and mixtures thereof.

8. The multi-layer biomimetic organ model of claim 1, wherein the gel layer further comprises at least one type of macrophages, dendritic cells, microbial cells, fibroblasts, endothelial cells, blood monocytes, pericytes, stem cells, immune cells, muscle cells, neural cells, or mixtures thereof.

9. The multi-layer biomimetic organ model of claim 1, wherein the epithelial cells are obtained from a healthy human organ or a chronically diseased human organ.

10. The multi-layer biomimetic organ model of claim 1, wherein the at least one agent delivered through the one or more of the at least one microchannel includes a pharmaceutical composition and the multi-layer biomimetic organ model further comprises
a bioanalytical platform for measuring biological responses of the layer of cells to the at least one agent.

11. The multi-layer biomimetic organ model of claim 1, further comprising
a bioanalytical platform for measuring biological responses of the layer of cells to the at least one agent in order to identify harmful agents.

12. The multi-layer biomimetic organ model of claim 1, wherein the gel layer disposed in the at least one chamber of the at least one chamber slab is perfused only by fluid flow from the at least one microchannel disposed in each of the at least two channel slabs.

13. A multi-layer biomimetic organ model comprising:
a body comprising
a first channel slab and a second channel slab, and
a chamber slab disposed therebetween;
a microchannel disposed in each of the first channel slab and the second channel slab;
a chamber disposed in the chamber slab, the chamber being exposed at a first surface of the chamber slab and exposed at a second surface of the chamber slab, an internal surface of the chamber, between the first surface and the second surface, being uninterrupted;
a first membrane disposed between the first channel slab and the chamber slab, the membrane having a first side facing the microchannel disposed in the first channel slab and a second side facing the chamber;
a second membrane disposed between the second channel slab and the chamber slab, the membrane having a first side facing the chamber and a second side facing the microchannel disposed in the second channel slab;
a first layer of cells coating at least the first side of the first membrane and a second layer of cells coating the second side of the second membrane;
a gel layer disposed in the chamber and configured to be anchored on the internal surface of the chamber of the chamber slab for adjusting contraction time of the gel layer; and
at least one device to deliver at least one agent through at least one of the microchannel disposed in each of the first channel slab and the second channel slab, wherein
the first layer of cells comprises epithelial cells and the second layer of cells comprises endothelial cells, and
the microchannel disposed in the first channel slab and the microchannel disposed in the second channel slab are in fluid communication through the first membrane, the second membrane, and the gel layer.

14. The multi-layer biomimetic organ model of claim 13, wherein the epithelial cells comprise pulmonary epithelial cells, hepatic epithelial cells, or renal epithelial cells, and the endothelial cells comprise endothelial cells from the same organ.

15. The multi-layer biomimetic organ model of claim 13, wherein at least one of the first layer of cells and the second layer of cells further comprises at least one type of macrophages, dendritic cells, microbial cells, or mixtures thereof.

16. A multi-layer biomimetic organ model comprising:
a body, having at least two channel slabs and at least one chamber slab;
at least one microchannel disposed in each of the at least two channel slabs;
at least one chamber disposed in the at least one chamber slab, the at least one membrane comprising from 0.6 µm to 8 µm pores;
at least one membrane disposed between at least one of the at least two channel slabs and the at least one chamber slab, the at least one membrane having a first side facing at least one microchannel of the one or more of the at least two channel slabs and a second side facing the at least one chamber of the at least one chamber slab;
a layer of cells coating at least the first side of the at least one membrane;
a gel layer disposed in the at least one chamber of the at least one chamber slab, the gel layer being configured to be anchored on a surface of the chamber slab for adjusting contraction time of the gel layer; and
at least one device to deliver at least one agent through one or more of the at least one microchannel, wherein
the layer of cells coating the first side of the at least one membrane comprising epithelial cells,
the at least one microchannel disposed in each of the at least two channel slabs are in fluid communication through the at least one membrane and the gel layer disposed in the at least one chamber of the at least one chamber slab, and
the gel layer is configured to be anchored on a surface of the at least one chamber slab for adjusting contraction time of the gel layer.

* * * * *